United States Patent
McCulloch et al.

(10) Patent No.: US 9,259,452 B2
(45) Date of Patent: Feb. 16, 2016

(54) DEACETYLASE INHIBITOR THERAPY

(71) Applicant: Celgene Corporation, Summit, NJ (US)

(72) Inventors: William McCulloch, Raleigh, NC (US); Richard L. Piekarz, Silver Spring, MD (US); Susan E. Bates, Bethesda, MD (US)

(73) Assignees: Celgene Corporation, Summit, NJ (US); The United States of America Department of Health and Human Services, Washington, DC (US)

( * ) Notice: Subject to any disclaimer, the term of this patent is extended or adjusted under 35 U.S.C. 154(b) by 0 days.

(21) Appl. No.: 14/590,709

(22) Filed: Jan. 6, 2015

(65) Prior Publication Data

US 2015/0182585 A1    Jul. 2, 2015

Related U.S. Application Data

(63) Continuation of application No. 11/759,471, filed on Jun. 7, 2007, now Pat. No. 8,957,027.

(60) Provisional application No. 60/909,780, filed on Apr. 3, 2007, provisional application No. 60/811,961, filed on Jun. 8, 2006.

(51) Int. Cl.
*A61K 38/15* (2006.01)
*A61K 33/00* (2006.01)
*A61K 33/06* (2006.01)
*A61P 35/00* (2006.01)
*A61K 31/19* (2006.01)
*A61K 33/14* (2006.01)

(52) U.S. Cl.
CPC ............. *A61K 38/15* (2013.01); *A61K 31/19* (2013.01); *A61K 33/00* (2013.01); *A61K 33/06* (2013.01); *A61K 33/14* (2013.01)

(58) Field of Classification Search
None
See application file for complete search history.

(56) References Cited

U.S. PATENT DOCUMENTS

| | | | |
|---|---|---|---|
| 4,977,138 A | 12/1990 | Okuhara et al. |
| 5,055,608 A | 10/1991 | Marks et al. |
| 5,175,191 A | 12/1992 | Marks et al. |
| 5,369,108 A | 11/1994 | Breslow et al. |
| 5,508,269 A | 4/1996 | Smith et al. |
| 5,510,270 A | 4/1996 | Fodor et al. |
| 5,545,522 A | 8/1996 | Van Gelder et al. |
| 5,556,752 A | 9/1996 | Lockhart et al. |
| 5,578,832 A | 11/1996 | Trulson et al. |
| 5,605,793 A | 2/1997 | Stemmer |
| 5,608,108 A | 3/1997 | Marks et al. |
| 5,700,811 A | 12/1997 | Breslow et al. |
| 5,716,785 A | 2/1998 | Van Gelder et al. |
| 5,767,068 A | 6/1998 | VanDevanter et al. |
| 5,773,474 A | 6/1998 | Breslow et al. |
| 5,776,905 A | 7/1998 | Gibbons et al. |
| 5,830,721 A | 11/1998 | Stemmer et al. |
| 5,837,458 A | 11/1998 | Minshull et al. |
| 5,891,636 A | 4/1999 | Van Gelder et al. |
| 5,932,616 A | 8/1999 | Breslow et al. |
| 6,117,679 A | 9/2000 | Stemmer |
| 6,391,640 B1 | 5/2002 | Minshull et al. |
| 6,403,555 B1 | 6/2002 | Skov et al. |
| 6,511,990 B1 | 1/2003 | Breslow et al. |
| 6,548,479 B1 | 4/2003 | Skov et al. |
| 6,706,686 B2 | 3/2004 | Long et al. |
| 6,777,217 B1 | 8/2004 | Schreiber et al. |
| 6,809,118 B2 | 10/2004 | Chung et al. |
| 6,828,302 B1 | 12/2004 | Skov et al. |
| 6,905,669 B2 | 6/2005 | DiMartino |
| 6,946,441 B2 | 9/2005 | Long et al. |
| 7,041,639 B2 | 5/2006 | Skov et al. |
| 7,056,883 B2 | 6/2006 | Ito et al. |
| 7,056,884 B2 | 6/2006 | Nakajima et al. |
| 7,148,204 B2 | 12/2006 | Bennett et al. |
| 7,171,311 B2 | 1/2007 | Dai et al. |
| 7,314,862 B2 | 1/2008 | Naoe et al. |
| 7,354,928 B2 | 4/2008 | Wang et al. |
| 7,396,665 B2 | 7/2008 | Ueda et al. |
| 7,470,722 B2 | 12/2008 | Malecha et al. |
| 7,488,712 B2 | 2/2009 | Yoshida et al. |
| 7,857,804 B2 | 12/2010 | McCaffrey et al. |
| 2003/0162293 A1 | 8/2003 | Chu et al. |
| 2004/0018968 A1 | 1/2004 | Sgouros et al. |
| 2004/0053820 A1 | 3/2004 | Nakajima et al. |
| 2004/0072735 A1 | 4/2004 | Richon et al. |

(Continued)

FOREIGN PATENT DOCUMENTS

| CA | 2317003 | 8/2001 |
|---|---|---|
| EP | 0352646 | 1/1990 |

(Continued)

OTHER PUBLICATIONS

Getting the Facts, "Peripheral T-Cell Lymphoma", Lymphoma Research Foundation (2011).*
Antos et al., "Dose-dependent blockade to cardiomyocyte hypertrophy by histone deacetylase inhibitors," *J Biol Chem* 278:28930-28937, 2003.
Archaya et al., "Rational development of histone deacetylase inhibitors as anticancer agents: a review," Mol Pharmacol 68(4):917-932, 2005.
Aron et al., "Depsipeptide (FR901228) induces histone acetylation and inhibition of histone deacetylase in chronic lymphocytic leukemia cells concurrent with activation of caspase 8-mediated apoptosis and down-regulation of c-FLIP protein," Blood, 102(2):652-658 (2003).

(Continued)

*Primary Examiner* — Abigail Fisher
*Assistant Examiner* — Frank Choi
(74) *Attorney, Agent, or Firm* — Jones Day

(57) ABSTRACT

The present invention relates to deacetylase inhibitor (e.g., histone deacetylase inhibitor) therapies and demonstrates that individuals with low electrolyte levels may have increased susceptibility to certain unwanted side effects such as cardiac side effects. In some embodiments, the invention provides methods of administering DAC or DAC inhibitor therapy that includes electrolyte supplementation.

40 Claims, No Drawings

(56) References Cited

U.S. PATENT DOCUMENTS

| | | |
|---|---|---|
| 2004/0077591 A1 | 4/2004 | Dangond |
| 2004/0127523 A1 | 7/2004 | Bacopoulos et al. |
| 2004/0228909 A1 | 11/2004 | Sarris et al. |
| 2005/0059682 A1 | 3/2005 | Rubinfeld |
| 2005/0070467 A1 | 3/2005 | Naoe et al. |
| 2005/0187148 A1 | 8/2005 | Naoe et al. |
| 2005/0187149 A1 | 8/2005 | Naoe et al. |
| 2005/0191713 A1 | 9/2005 | Sasakawa et al. |
| 2005/0222013 A1 | 10/2005 | Jung et al. |
| 2005/0272647 A1 | 12/2005 | Yamaji et al. |
| 2005/0288227 A1 | 12/2005 | Marks et al. |
| 2006/0018921 A1 | 1/2006 | Levenson et al. |
| 2006/0019883 A1 | 1/2006 | Kronblad et al. |
| 2006/0100140 A1 | 5/2006 | Dent et al. |
| 2006/0106049 A1 | 5/2006 | Odenike |
| 2006/0128660 A1 | 6/2006 | Rajski et al. |
| 2006/0135413 A1 | 6/2006 | Naoe et al. |
| 2006/0223747 A1 | 10/2006 | Ito et al. |
| 2006/0270016 A1 | 11/2006 | Holm |
| 2007/0015787 A1 | 1/2007 | Bruncko et al. |
| 2007/0110719 A1 | 5/2007 | Holm |
| 2007/0129290 A1 | 6/2007 | Or et al. |
| 2007/0148228 A1 | 6/2007 | Cumming et al. |
| 2007/0292512 A1 | 12/2007 | Leonard et al. |
| 2008/0214446 A1 | 9/2008 | Okada et al. |
| 2008/0233562 A1 | 9/2008 | Sasakawa et al. |
| 2009/0186382 A1 | 7/2009 | Verdine et al. |
| 2009/0209616 A1 | 8/2009 | Verdine et al. |
| 2009/0221473 A1 | 9/2009 | Chan et al. |
| 2010/0093610 A1 | 4/2010 | Vrolijk et al. |

FOREIGN PATENT DOCUMENTS

| | | |
|---|---|---|
| EP | 1010705 | 6/2000 |
| EP | 1426054 | 6/2004 |
| JP | 7(1995)-64872 | 7/1995 |
| JP | 11-335375 | 12/1999 |
| JP | 2001-348340 | 12/2001 |
| WO | WO 98/39965 | 9/1998 |
| WO | WO 98/40080 | 9/1998 |
| WO | WO 98/43650 | 10/1998 |
| WO | WO 00/21979 | 10/1999 |
| WO | WO 00/71703 | 11/2000 |
| WO | WO 01/18171 | 3/2001 |
| WO | WO 01/38322 | 5/2001 |
| WO | WO 01/42282 | 6/2001 |
| WO | WO 01/70675 | 9/2001 |
| WO | WO 02/06307 | 1/2002 |
| WO | WO 02/15921 | 2/2002 |
| WO | WO 02/20817 | 3/2002 |
| WO | WO 02/22577 | 3/2002 |
| WO | WO 02/30879 | 4/2002 |
| WO | WO 02/086498 | 4/2002 |
| WO | WO 02/97053 | 5/2002 |
| WO | WO 02/055017 | 7/2002 |
| WO | WO 02/055688 | 7/2002 |
| WO | WO 02/085400 | 10/2002 |
| WO | WO 02/090534 | 11/2002 |
| WO | WO 03/015810 | 2/2003 |
| WO | WO 03/017763 | 3/2003 |
| WO | WO 03/024442 | 3/2003 |
| WO | WO 03/035843 | 5/2003 |
| WO | WO 03/053468 | 7/2003 |
| WO | WO 03/070188 | 8/2003 |
| WO | WO 03/083067 | 10/2003 |
| WO | WO 03/084611 | 10/2003 |
| WO | WO 03/088954 | 10/2003 |
| WO | WO 03/103613 | 12/2003 |
| WO | WO 2004/009771 | 1/2004 |
| WO | WO 2004/017996 | 3/2004 |
| WO | WO 2004/024160 | 3/2004 |
| WO | WO 2004/062654 | 7/2004 |
| WO | WO 2004/064727 | 8/2004 |
| WO | WO 2004/074478 | 9/2004 |
| WO | WO 2004/096289 | 11/2004 |
| WO | WO 2004/098495 | 11/2004 |
| WO | WO 2005/000282 | 1/2005 |
| WO | WO 2005/000289 | 1/2005 |
| WO | WO 2005/000332 | 1/2005 |
| WO | WO 2005/009961 | 2/2005 |
| WO | WO 2005/018578 | 3/2005 |
| WO | WO 2005/023179 | 3/2005 |
| WO | WO 2005/027842 | 3/2005 |
| WO | WO 2005/030239 | 4/2005 |
| WO | WO 2005/051430 | 6/2005 |
| WO | WO 2005/052143 | 6/2005 |
| WO | WO 2005/053609 | 6/2005 |
| WO | WO 2005/058298 | 6/2005 |
| WO | WO 2005/079827 | 9/2005 |
| WO | WO 2005/085864 | 9/2005 |
| WO | WO 2005/087206 | 9/2005 |
| WO | WO 2005/105055 | 11/2005 |
| WO | WO 2005/105066 | 11/2005 |
| WO | WO 2005/115149 | 12/2005 |
| WO | WO 2005/117930 | 12/2005 |
| WO | WO 2006/027346 | 3/2006 |
| WO | WO 2006/055621 | 5/2006 |
| WO | WO 2006/060382 | 6/2006 |
| WO | WO 2006/060429 | 6/2006 |
| WO | WO 2006/129105 | 12/2006 |
| WO | WO 2007/009539 | 1/2007 |
| WO | 2007040522 | 4/2007 |
| WO | WO 2007/040522 | 4/2007 |
| WO | WO 2007/058896 | 5/2007 |
| WO | WO 2007/061939 | 5/2007 |
| WO | WO 2007/145704 | 12/2007 |
| WO | WO 2007/146730 | 12/2007 |
| WO | WO 2008/013589 | 1/2008 |

OTHER PUBLICATIONS

Barbey et al. "Effect of arsenic trioxide on QT interval in patients with advanced malignancies," *J Clin Oncol* 21:3609-3615, 2003.
Barbour et al., "Studies on measurement of plasma magnesium: application of the Magon dye method to the "Monarch" centrifugal analyzer," Clin Chem 34:2103, 1998.
Bates et al., "Final Clinical Results of a Phase 2 NCI Multicenter Study of romidepsin in Recurrent Cutaneous T-Cell Lymphoma (Molecular Analyses Included)," ASH Annual Meeting Abstracts, 112(11): p. 1568 (2008).
Bednar et al.,"Torsades de pointes associated with nonantiarrhythmic drugs and observations on gender and QTc," *Am J Cardiol* 89:1316-1319, 2002.
Bednar el al., "The QT interval," *Prog Cardiovasc Dis* 43:1-45, 2001.
Berge et al., "Pharmaceutical Salts," J Pharm Science 66:1-19, 1977.
Bhalla, "Epigenetic and chromatin modicifers as targeted therapy of hematologic malignancies," J Clin Oncol, 23(17):3971-3993 (2005).
Bishton et al., "Epigenetic target in hematological malignancies: combination therapies with HDAC's and demethylating agents," Expert Rev Anticancer Ther, 7(10):1439-1449 (2007).
Bogden et al., "Growth of Human Tumor Xenografts Implanted under the Renal Capsule of Normal Immunocompetent Mice," Exp Cell Biol 47:281-293 (1979).
Bolden et al., "Anticancer activities of histone deacetylase inhibitors," Nat Rev Drug Discovery, 5(9):769-784 (2006).
Borer et al.,"Real-time radionuclide cineangiography in the noninvasive evaluation of global and regional left ventricular function at rest and during exercise in patients with coronary-artery disease," *N Eng J Med* 296:839-844, 1977.
Budillon et al., "Growth arrest, apoptosis and potentiation of 5-fluorouracil and Raltitrexed cytotoxic effect induced by histone deacetylase inhibitor SAHA in colorectal cancer cells," Eur J Cancer 38:S29 (2002).
Bundgaard et al., "Means to enhance penetration," *J Drug Deliver Rev* 8:1-38, 1992.
Butler et al., "Suberoylanilide Hydroxamic Acid, an Inhibitor of Histone Deacetylase, Suppresses the Growth of Prostate Cancer Cells in Vitro and in Vivo," Cancer Res 60:5165-5170 (2000).

(56) References Cited

OTHER PUBLICATIONS

Byrd et al., "A phase 1 and pharmacodynamic study of depsipeptide (FK228) in chronic lymphocytic leukemia and acute myeloid leukemia," Blood, 105(3):959-967 (2005).
Byrd et al., "Depsipeptide (FR901228): a novel therapeutic agent with Selective in vitro activity against human B-cell chronic lymphocytic leukemia cells ," Blood, 94(4):1401-1408 (1999).
Cardinale et al., "Myocardial injury revealed by plasma troponin I in breast cancer treated with high-dose chemotherapy," *Ann Oncol* 13:710-715, 2002.
Catley et al., "Aggresome induction by proteasome inhibitor bortezpmib and {alpha}-tubulin hyperacetylation by tubulin deacetylase (TDAC) inhibitor LBH589 are synergistic in myeloma cells," Blood 108(10):3441-3449 (2006).
Chan et al., "Depsipeptide (FR901228, NSC-630176) pharmacokinetics in the rat by LC/MS/MS ," Invest New Drugs,15(3):195-206 (1997).
Cheson et al., "New Drugs for the Treatment of Chronic Lymphocytic Leukemia," Reviews Clin Exp Hematol 4(2):145-166 (2000).
Chunrong et al.,"The proteasome inhibitor bortezomib interacts synergistically with histone deacetylase inhibitors to induce apoptosis in Bcr/Abl+ cells sensitive and resistant to STI571," *Blood* 102(10):3765-3774.
Conway et al., "Vincristine-and Cisplatin-induced Apoptosis in Human Retinoblastoma. Potentiation by Sodium Butyrate," Eur J Cancer, 34(11):1741-1748 (1998).
Curtin M., "Current patent status of histone deacetylase inhibitors," *Expert Opnin Ther Patents* 12(9):1375-1384, 2002.
Dai et al., "Interactions between bortezomib and romidepsin and belinostat in chronic lymphocytic leukemia cells ," Clin Cancer Res, 14(2):549-558 ( 2008).
Das, "QT interval and repolarization time in patients with intraventricular conduction delay," *J Electrocardiol* 23:49-52, 1990.
Database Biosis Online, AN-PREV200400024248, XP-002342749, "Anti-Tumor Efficacy of Four Different Histone Deacetylase Inhibitors on Hepatoma Cells in Vitro", 2003 (Abstract No. T1786).
Dokmanovic & Marks, "Prospects: histone deacetylase inhibitors ," J Cell Biochem, 96(2):293-304 (2005).
Duvic et al., Phase II Trial of Oral Suberoylanilide Hydroxamic Acid for Cutaneious T-Cell Lymphoma (CTCL) and Periperhal T-Cell Lymphoma (PTCL) *Blood* 102:179a, 2003.
Ewer et al. "Cardiotoxicity in patients receiving transtuzumab (Herceptin): primary toxicity, synergistic or sequential stress, or surveillance artifact?," Seminars Oncol 26:96-101, 1999.
Ewer et al., "Type II chemotherapy-related cardiac dysfunction: time to recognize a new entity,"*J Clin Oncol* 23:2900-2902, 2005.
Fiebig et al., "Bcl-XL is qualitatively different from and ten times more effective than Bc1-2 when expressed in a breast cancer cell line," Cancer, 6:213 (2006).
Findley et al., "Expression and Regulation of Bcl-2, Bcl-xl, and Bax Correlate With p53 Status and Sensitivity to Apoptosis in Childhood Acute Lymphoblastic Leukemia," Blood, 89(8): 2986-2993 (1997).
Finnin et al., "Structures of a histone deacetylase homologue bound to the TSA and SAHA Inhibitors," Nature, 401(6749):188-193 (1999).
Fischer et al., 41$^{st}$ Annual Meeting of the American Society of Clinical Oncology, Abstr # 3106 (2005).
Fukumura et al., "A sensitive transcriptome analysis method that can detect unknown transcripts," Nucl Acids Res 31(16):e94 (2003).
Furumai et al., "Potent histone deacetylase inhibitors built from trichostatin A and cyclic tetrapeptide antibiotics including trapoxin," *PNAS USA* 98(1):87-92, 2001.
Furumai et al.," FK228 (depsipeptide) as a natural prodrug that inhibits class I histone deacetylases," Cancer Res, 62(17):4916-4921 (2002).
Garcia-Manero et al., "Phase 1/2 study of the combination of 5-aza-2'-deoxycytidine with valporic acid in patients with leukemia ," Blood, 108(10):3271-3279 (2006).

Geldof et al., "Cytotoxicity and neurocytotoxicity of new marine anticancer agents evalucated using in vitro assays," Cancer Chemother & Pharmacol 44(4):312-318 (1999).
Goodman et al. (Eds.), Chapter 198: "Principles of Cancer Therapy", Cecil's Textbook of Medicine (21$^{st}$ Edition, vol. 1, W.B. Saunders Company, 2000, pp. 1060-1074.
Gore et al., "Combined DNA methyltransferase and histone deacetylase inhibition in the treatment of myeloid neoplasms," Cancer Res, 66(12):6361-6369 (2006).
Gore et al., "Impact of the putative differentiating agent sodium phenylbutyrate on myelodysplastic syndromes and acute myeloid leukemia ," Clin Cancer Res, 7(8):2330-2339 (2001).
Gottdjener et al.,"Cardiotoxicity associated with high-dose cyclophosphamide therapy," *Arch Intern Med* 141:758-763, 1981.
Gu et al., "Activation of p53 sequence-specific DNA binding by acetylation of the p53 C-terminal domain," *Cell* 90:595-606, 1997.
Han et al., "Apicidin, a Histone Deacetylase Inhibitor Inhibits Proliferation of Tumor Cells via Induction of p21 WAF1/Cip1 and Gelsolin," Cancer Res 60(21):6068-6074 (2000).
Harrison et al., "High Response Rates with the Combination of Bortezomib, Dexamethasone and the Pan-Histone Deacetylase Inhibitor Romidepsin in Patients with Relapsed or Refractory Multiple Myeloma in Phase I/II Clinical Trial," ASH Annual Meeting Abstracts, 112(11):3698 (2008).
Herman et al., "Use of cardiac troponin T levels as an indicator of doxorubicin-induced cardiotoxicity," *Cancer Res* 58:195-197, 1998.
Herman et al., "Correlation between serum levels of cardiac troponin-T and the severity of the chronic cardiomyopathy induced by doxorubicin," *J Clin Oncol* 17:2237-2243, 1999.
Inoue et al., "Subrenal capsule assay-an experimental study and clinical application to chemosensitivity tests," Gan to Kagaku Ryoho 14(5Pt2):1629-1635 (1987) (Abstract).
Jones & Baylin, "The Epigenomics of Cancer," Cell 128:683-692 (2007).
Jones & Baylin, "The fundamental role of epigenetic events in Cancer,"Nat Rev Genet, 3(6):415-428 (2002).
Jung et al., "Amide Analogues of Trichostatin A as Inhibitors of Histone Deacetylase and Inducers of Terminal Cell Differentiation," J Med Chem US 42(22):4669-4679 (1999).
Kahn et al., "Total Synthesis of the Antitumor Depsipeptide FR-901,228," J Am Chem Soc 118:7237-7238, (1996).
Kano et al., "The Joint Meeting of the 64$^{th}$ Annual Meeting of the Japanese Society of Hematology and the 44$^{th}$ Annual Meeting of the Japanese Society of Clinical Hematology," Japanese J Clin Hematology 43(8):116 (2002).
Kawamoto et al., "Expression Profiling by iAFLP: A PCR-Based Method for Genome-Wide Gene Expression Profiling," Genome Res 12:1305-1312 (1999).
Keefe, "The cardiotoxic potential of the 5-HT(3) receptor antagonist antiemetics: is there cause for concern?," *Oncologist* 7:65-72, 2002.
Kelly et al., "Phase I clinical trial of histone deacetylase inhibitor: suberoylanilide hydroxamic acid administered intravenously," *Clin Cancer Res* 9:3578-3588, 2003.
Khan et al., "Analysis of histone deacetylase inhibitor, depsipeptide (FR901228), effect on multiple myeloma ," Br J Haematol, 125(2):156-161 (2004).
Kim et al., "Clinically significant responses Achieved with Romidepsin in Treatment-Refractory Cutaneous T-Cell Lymphoma: Final Results from a Phase 2B, International, Multicenter, Registration Study," ASH Annual Meeting Abstracts, 112(11):263 (2008).
Kim et al., "Oxamflatin is a novel antitumor compound that inhibits mammalian histone deacetylase," Oncogene 18:2461-2470, 1999.
Kimura et al., "New enzymatic method with tryptophanase for determining potassium in serum," Clin Chem38:44, 1992.
Kisselev & Goldberg, "Proteasome inhibitors: from research tools to drug candidates," Chem Biol 8:739-758 (2001).
Kitazono et al., "Adenovirus HSV-TK Constuct with Thyroid-Specific Promoter: Enhancement of Activity and Specificity with Histone Deacetylase Inhibitors and Agents Modulating the Camp Pathway," Int J Cancer 99:453-459 (2002).
Kitazono et al., "Enhanced Adenovirus Transgene Expression in Malignant Cells Treated with the Histone Deacetylase Inhibitor FR901228," Cancer Res 61:6328-6330 (2001).

(56) References Cited

OTHER PUBLICATIONS

Kitazono et al., "Low Concentrations of the Histone Deacetylase Inhibitor, Depsipeptide (FR901228), Increase Expression of the Na/I Symporter and Iodine Accumulation in Poorly Differentiated Thyroid Carcinoma Cells," J Clin Endocrin 86(7):3430-3435 (2001).
Kitazono et al., Proc Amer Assoc Cancer Res Annual 43:799 (2002) (Abstract only).
Klimek et al., "Tolerability, pharmacodynamics, and pharmacokinetics studies fo depsipeptide (romidepsin) in patients with acute myelogenous leukemia or advanced myelodysplastic syndromes," Clin Cancer Res, 14(3):826-832 (2008).
Klisovic et al., "Depsipeptide (FR9801228) Inhibits Proliferation and Induces Apoptosis in Primary and metastatic Human Uveal Melanoma Cell Lines," Invest Ophthalmol Vis Sci, 44(6):2390-2398 (2003).
Koch et al.,"Evaluation of a direct potentiometric method for sodium and potassium used in the Du Pont aca," Clin Chem 29:1090, 1983.
Komatsu et al., "Cyclic Cyfroxamic-acid-containing Peptide 31, a Potent Syntheic Histone Deacetylase Inhibitor with Antitumor Activity," Cancer Res 61(11):4459-4466 (2001).
Kook et al., "Cardiac hypertrophy and histone deacetylase-dependent transcriptional repression mediated by the atypical homeodomain protein Hop,"*J Clin Invest* 112:863-871, 2003.
Kosugi et al., "In vivo Effects of a Histone Deacetylase Inhibitor, FK228, on Human Acute Promyelocytic Leukemia in NOD/Shi-scid/scid Mice," Japanese J Cancer Res 92(5):529-536 (2001).
Kuendgen et al., "Treatment of myelodysplastic syndromes with valproic acid alone or in combination with all-trans retinoic acid," Blood, 104(5):1266-1269 (2004).
Lee et al., "MS-275, a histone deacetylase inhibitor, selectively induces transforming growth factor beta type II receptor expression in human breast cancer cells," *Cancer Res* 61(3):931-934 (2001).
Lenihan et al., "Cardiac toxicity of alemtuzumab in patients with mycosis fungoides/Sézary syndrome," *Blood* 104:655-658, 2004.
Li et al. "Total Synthesis of the Antitumor Depsipeptide FR-901,228," *J Am Chem Soc* 118(30):7237-7238, 1996.
Liakopoulou et al., "Stimulation of Fetal Hemoglobin Production by Short Chain Fatty Acids," Blood, 86:3227 (1995).
Maeda et al., "Up-regulation of costimulatory/adhesion molecules by histone deacetylase ihibitors in acute myeloid leukemia cells," Blood, 96(12):3847-3856 (2000).
Magner et al., "Activation of MHC class I, II, and CD40 gene expression by histone deacetylose inhibitors ," J Immunol, 165(12):7017-7024 (2000).
Marks et al., "Histone deacetylase inhibitors: Inducers of differentiation or apoptosis of transformed cells," J Natl Cancer Inst, 92(15):1210-1216 (2000).
Marshall et al., "A phase I trial of depsipeptide (FR901228) in patients with advanced cancer ," J Exp Ther Oncol, 2(6):325-332 (2002).
Mertins et al., Proc Amer Assoc Cancer Res Annual Meetins 40:623 (1999).
Missov et al., "Cardiac troponin I in patients with hematologic malignancies," *Coron Artery Dis* 8:537-541, 1997.
Mitsiades et al., "Transcriptional signature of histone deacetylase inhibition in multiple myeloma: biological and clinical implications," Proc Natl Acad Sci USA, 101(2):540-545 (2004).
Molife et al.,"Phase II study of FK228 in patients with hormone refractory prostate cancer (HRPC)," J Clin Oncol (Meeting Abstracts), 24(18 Suppl):14554 (2006).
Morgan et al., "Hypomagnesemia and hypocalcemia in mycosis fungoides: a retrospective case series," *Lek Lynphoma* 43:1297-1302, 2002.
Morganroth, "Relations of QTc prolongation on the electrocardiogram to torsades de pointes: definitions and mechanisms,"*Am J Cardiol* 72:B10-B13, 1993.
Moss, "Measurement of the QT interval and the risk associated with QTc interval prolongation: a review," *Am J Cardiol* 72:23B-25B, 1993.

Murata et al., "Apoptotic Cytotoxic Effects of a Histone Deacetylase Inhibitor, FK228, on Malignant Lymphoid Cells," Japanese J Cancer Res 91:1154-1160 (2000).
Nakajima et al., ", FR901228, a potent antitumor antibiotic, is a novel histone det 1 cetylose inhibitor," Exp Cell Res, 241(1)126-133 (1998).
Nebbioso et al., "Tumor-selective action of HDAC inhibitors involves TRAIL induction in acute myeloid leukemia cells," Nat Med, 11(1):77-84 (2005).
Nebozhyn et al., "Quantitative PCR on 5 genes reliably Identifies CTCL patients with 5% to 99% circulating tumor cells with 90% accuracy," Blood, 107(8):3189-3196 (2006).
Newbold et al., "Characterisation of the novel apoptotic and therapeutic activities of the histone deacetylase inhibitor romidepsin," Mol Cancer Ther, 7(5):1066-1079 (2008).
Niesvizky et al., "Multicenter Phase II Trial of the Histone Deacetylase Inhibitor Depsipeptide (FK228) for the Treatment of Relapsed or Refractory Multiple Myeloma (MM),".
Blood ASH Annual Meeting Abstracts, 106(11):2574 (2005).
Nishimura et al., "A New Antitumor Antibiotic, FE900840," J Antibiot XLII(4):553-557 (1989).
Nuijen et al., "Development of a lyophilized parenteral pharmaceutical formulation the investicational polypeptide marine anticancer agent kahalalide F.," Medline (2001) XP-002206588.
Odenike et al., "Histone deacetylase inhibitor romidepsin has differential activity in core binding factor acute myeloid leukemia," Cancer Res, 14(21):7095-7101 (2008).
Paoluzzi et al., "Romidepsin and belinostat synergize the antineoplastic effect of bortezomib in mantle cell lymphoma," Clin Cancer Res, 16(2):554-565 (2010).
Peart et al., "Identification and functional significance of genes regulated by structurally different histone deacetylose inhibitors ," Proc Natl Acad Sci USA, 102(10):3697-3702 (2005).
Peart et al., "Novel mechanisms of apoptosis induced by histone deacetylase inhibitors ," Cancer Res, 63(15):4460-4471 (2003).
Pei et al., "Synergistic induction of oxidative injury and apoptosis in human multiple myeloma cells by the proteasome inhibitor bortezpmib and histone deacetylase inhibitors," Clin Cancer Res, 10(11):3839-3852 (2004).
Piekarz et al., "A Review of Depsipeptide and Other Histone Deacetylase Inhibitors in Clinical Trials," Curr Pharm Des 10:2289-2298 (2004).
Piekarz et al., "Cardiac studies in patients treated with depsipeptide, FK228,in a phase II trial for T-cell lymphoma," Clin Cancer Res, 12(12):3762-3773 (2006).
Piekarz et al., "Completion of the First Cohort of Patients with Cutaneous T-Cell Lymphoma Enrolled on a Phase II Trial of Depsipeptide ," ASH Annual Meeting Abstracts,106(11):231 (2005).
Piekarz et al., "Epigenetic modifiers: basic understanding and clinical development," Clin Cancer Res, 15(12):3918-3926 (2009).
Piekarz et al., "Inhibitor of histone deactylation, depsipeptide (FR901228), in the treatment of peripheral and cutaneous T-cell lymphoma: a case report," Blood, 98(9):2865-2868 (2001).
Piekarz et al., "Phase II Multi-Institutional Trial of the Histone Deacetylase Inhibitor Romidepsin As Monotherapy for Patients With Cutaneous T-Cell Lymphoma," J Clin Oncol, 27(32):5410-5417 (2009).
Piekarz et al., "Results of a Phase 2 NCI Multicenter Study of Romidepsin in Patients with Relapsed Peripheral T-Cell Lymphoma (PTCL)," ASH Annual Meeting Abstracts 112(11):1567 (2008).
Piekarz et al., "T-cell lymphoma as a model for the use of histone deacetylase inhibitors in cancer therapy: impact of depsipeptide on molecular markers, therapeutic targes, and mechanisms of resistance," Blood , 103(12):4636-4643 (2004).
Piekarz, R., et al, "Update of the NCI multiinstutional phase II trial of romidepsin, FK228,for patients with cutaneous or peripheral T-cell lymphoma,". J Clio Oncol (Meeting Abstracts), 2007.25(18 suppl): p. 8027 (2007).
Prince et al., "Clinical studies of histone deacetylase inhibitors," Clin Cancer Res, 15(12):3958-3969 (2009).
Program of the 4th Japanese Foundation for Cancer Research, International Symposium on Cancer Therapy (ISCC), Feb. 12, 1999.

(56) References Cited

OTHER PUBLICATIONS

Qui et al., "Histone deacetylase inhibitors trigger a G2 checkpoint in normal cells that is defective in tumor cells," *Mol Biol Cell* 11:2069-2083, 2000.
Rasheed et al., "Histone deacetylase inhibitors in cancer therapy," Expert Opin Investig Drugs, 16(5):659-678 (2007).
Rehak et al., "Modified magnesium method in the aca III: elimination of interference by bilirubin," *Clin Chem* 35:1031, 1989.
Richon et al., "Histone Deacetylase Inhibitors: A New Class of Potential Therapeutic Agents for Cancer Treatment," Clin Cancer Res 8(3):662-664 (2002).
Richon et al., "Histone deacetylasei inhibitor selectively induces p21WAFI expression and gene-associated histone acetylation,"Proc Natl Acad Sci USA, 97(18):10014-10019 (2000).
Robey et al.," Increased MDRI expression in normal and malignant peripheral blood mononuclear cells obtained from patients receiving depsipeptide (FR901228, FK228, NSC630176)," *Clin Cancer Res* 12(5):1547-1555, 2006.
Roden, "Drug-induced prolongation of the QT interval," *N. Eng J Med* 350:1013-1022, 2004.
Rowinsky et al., "Cardiac monitoring in phase I trials of a novel histone deacetylase inhibitor LAQ824 in patients with advanved solid tumors and hematologic malignancies," *J Clin Oncol* 22:Abstract #3131, 2005.
Roychowdhury et al., "Selective efficacy of depsipeptide in a xenograft model of Epstein-Barr virus-positive lymphoproliferative disorder ," J Natl Cancer Inst, 96(19):1447-1457 (2004).
Ryan et al.,"Phase I and pharmacokinetic study of MS-275, a histone deacetylase inhibitor, in patients with advanced and refractory solid tumors or lymphoma," *J Clin Oncol* 23:3912-3922, 2005.
Sagie et al., "An improved method for adjusting the QT interval for heart rate (the Framingham Heart Study)," *Am J Cardiol* 70:797-801, 1992.
Saito et al., "A synthetic inhibitor of histone deacetylase, MS-27-275, with marked in vivo antitumor activity against human tumors," *PNAS* USA 96:4592-4597, 1999.
Sakai et al., "MBD3 and HDACI,two components of the NuRDcomplex, are localized at Aurora-A-positive centrosomes in M phase,"J Biol Chem, 277(50):48714-48723 (2002).
Sandor et al., "P21-dependent G arrent with downregulation of cyclin D1 upregulation of cyclin E by the histone deacetylase inhibitor FR901228," Br J Cancer 83(6):817-825, (2000).
Sandor et al., "Phase I trial of the histone deacetylase Inhibitor, depsipeptide (FR901228, NSC 630176), in patients with refractory neoplasms ," Clin Cancer Res, 8(3):718-728 (2002).
Sasakawa et al., "Effects of FK228, a novel histone deacetylase inhibitor, on human lymphoma U-937 cells in vitro and in vivo," Biochem Pharmacol, 64(7):1079-1090 (2002).
Savage O.A., Clinical Trial Information published May 2, 2005, retrieved from Internet URL <<http??www.cancer.gov/clinicaltrials/CCCWFU-71103#RegistryInfo_CDR0000433042>>.
Sawa et al., "Anti-tumor effects of Hitone deacetylase inhibitors against human glioma cells," Proc of Japanese Cancer Assoc 60:597 (2001) (w/English translation).
Sawa et al., "Histone deacetylase Inhibitor, FK228, Induces apoptosis and suppresses cell roliferation of human glioblastoma cells in vitro and in vivo ," Acta Neuropathol (Berlin), 07(6):523-531 (2004).
Schiller et al., "Recommendations for quantitation of the left ventricle by two-dimensional echocardiography. American Society of Echocardiography Committee on Standards, Subcommittee on Quantitation of Two-Dimensional Echocardiograms,"*J Am Soc Echocardiogr* 2:358-367, 1989.
Schrump et al., "Clinical and molecular responses in lung cancer patients receiving romidepsin," Clin Cancer Res, 14(1):188-198 (2008).
Schwartsmann et al., "Marine organisms as a source of new anticancer agents," The Lancet Oncology 2(4):221-225 (2001).
Seidman et al., "Cardiac Dysfunction in the Trastuzumab Clinical Trials Experience," *J Clin Oncol* 20:121501221, 1999.
Shan et al., "Anthracycline-induced cardiotoxicity," *Ann Intern Med* 125:47-58, 1996.
Shiraga et al., "Identification of cytochrome P450 enzymes involved in the metabolism of FK228, a potent histone deacetylase inhibitor, in human liver microsomes," *Biol Pharm Bull* 28:124-129, 2005.
Shisukuda et al., "Effect of a histone deacetylase inhibitor on human cardiac mass," *Cardiovasc Drugs Ther* 19:89-90, 2005.
Sierra-Galan et al., "Qualitative Assessment of Regional Left Ventricular Function Can Predict MRI or Radionuclitide Ejection Fraction: An Objective Alternative to Eyeball Estimates," *J Cardiovasc Magn Reson* 5:4510463, 2003.
Singal et al., "Doxorubicin-induced cardiomyopathy," *N. Eng J Med* 339:900-905, 1998.
Speyer, "Cardiac dysfunction in the trastuzumab clinical experience," *J Clin Oncol* 20:1156-1157, 2002.
Sreedharan et al., "Relevance of circadian closing time for the tolerability of germcitabine as a single agent of combined with cisplatin in mice," Proc Amer Assoc Cancer Res 44(2 ed.):742 (2003) (XP-001154773).
Stadler et al., "A phase II study of depsipeptide in refractory metastatic renal cell cancer" Clin Genitourin Cancer, 5(1):57-60 (2006).
Steele et al., "A phase I pharmacokinetic and pharmacodynamic study of the histone deacetylase inhibitor PXD101 in patients with advanced solid tumors," *J Cliln Oncol* 22:3035, 2005.
Su et al., "A phase II study of single agent depsipeptide (DEP) in patients (pts) with radioactive iodine (RAI)-refractory, metastatic,thyroid carcinoma: Preliminary toxicity and efficacy experience," J Clin Oncol (Meeting Abstracts), 24(18 Suppl):5554 (2006).
Su et al., "A novel histone deacetylase inhibitor identified by high-throughput transcriptional screening of a compound library," Cancer Res 60:3137-3142, 2000.
Sundaram et al., "Risk stratification and epidemiology of sudden death," *Curr Cardiol Rep* 6:333-338, 2004.
Sutheesophon et al., "Histone deacetylase inhibitor depsipeptide (FK228) induces apoptosis in leukemic cells by facilitating mitochondrial translocation of Bax, which is enhanced by the proteasome Inhibitor bonezpmib," Acta Haematol, 115(1-2):78-90 (2006).
Suzuki et al., "Synthesis and histone deacetylase inhibitory activity of new benzamide derivatives," J Med Chem 42(15):3001-3003, 1999.
Swain et al., "Congestive heart failure in patients treated with doxorubicin: a retrospective analysis of three trials," *Cancer* 97:2869-2879, 2003.
Ueda et al., "Action of FR901228, a novel antitumor bicyclic depsipeptide produced by Chromobacterium violaceum No. 968, on Ha-ras transformed NIH3T3 cells ," Biosci Biotechnol Biochem, 58(9):1579-1583 (1994).
Ueda et al., "Expression of a full-length cDNA for the human "MDR1" gene confers resistance to colchicines, doxorubicin, and vinblastine," PNAS USA 84:3004 (1987).
Ueda et al., "FR901228, a novel antitumor bicyclic depsipeptide produced by Chromobacterium violaceum No. 968. I. Taxonomy, fermentation, isolation, physico-chemical and biological properties, and antitumor activity," J Antibiot (Tokyo),47:301-310, (1994).
Ueda et al., "FR901228, a Novel Antitumor Bicyclic Depsipeptide Produced by Chromobacterium violaceum No. 968," J Antibiot (Tokyo) 47:315-323 (1994).
Vrana et al., "Induction of apoptosis in U937 human leukemia cells by suberoylanilide hydroxamic acid (SAHA) proceeds through pathways that are regulated by Bcl-2/Bcl-XL, c-Jun, and p21CIPI, but independent of p53," Oncogene, 18(50):7016-7025 (1999).
Wang et al., "Fungal metabolite FR901228 inhibits c-Myc Fas ligand expression," Oncogene 17:1503-1508 (1998).
Watanabe et al., "Induction of autophagy in malignant rhabdoid tumor cells by the histone deacetylase inhibitor FK228 through AIF translocation ," Int J Cancer,124(1):55-67 (2009).
Weidle et al. "Inhibition of Histone Deacetylases: A New Strategy to Target Epigentic Modifications for Anticancer Treatment," Anticancer Res 20:1471-1486 (2000).

(56) References Cited

OTHER PUBLICATIONS

Whitehead et al., "Phase II trial of depsipeptide (NSC-630176) in colorectal cancer patients who have received either one or two prior chemotherapy regimens for nwrARrux or locally advanced, unresectable disease: A Southwest Oncology Group study," J Clin Oncol (Meeting Abstracts), 24(18 Suppl):3598 (2006).

Whittaker et al., "International multicenter phaSe H study of the HDAC inhibitor (HDAC) depsipeptide (FK228) in cutaneous T-cell lymphoma (CTCL): Interim report," J Clin Oncol (Meeting Abstracts), 24(18 Suppl):3063 (2006).

Xiao et al., "Efflux of Depsipeptide FK228(FR901228, NSC-630176) Is Mediated by P-Glycoprotein and Multidrug Resistance-Associate Protein 1," J Pharm & Exp Therapeutics 313(1):268-276(2005).

Xiao et al., "Identification of thiols and glutathione conjugates of depsipeptide FK228 (FR901228), a novel hostone protein deacetylase inhibitor, in the blood," Rapid Commun Mass Spectrom 17:757-766 (2003).

Yoshida et al., "Trichostatin A and trapoxin: novel chemical probes for the role of histone acetylation in chromatin structure and function," *Bioassays* 17:423-430, 1995.

Yu et al., "The proteasome inhibitor bortezpmib interacts synergistically with histone deacetylase inhibitors to induce apoptosis in Bcr/Abl+ cells sensitive and resistant to STI571," Blood, 102(10):3765-3774 (2003).

Zhang et al., "Class II Histone Deacetylases Act as Signal-Responsive Repressors of Cardiac Hypertrophy," *Cell* 110:4790488, 2002.

Non final office action for U.S. Appl. No. 13/624,807 dated Oct. 22, 2014.

Final office action for U.S. Appl. No. 13/624,807 dated May 26, 2015.

Advisory action for U.S. Appl. No. 13/624,807 dated Sep. 16, 2015.

\* cited by examiner

DEACETYLASE INHIBITOR THERAPY

This application is a continuation of U.S. application Ser. No. 11/759,471, filed Jun. 7, 2007, which claims priority to U.S. provisional application Ser. No. 60/811,961, filed Jun. 8, 2006, and U.S. provisional application Ser. No. 60/909,780, filed Apr. 3, 2007, which are incorporated herein by reference in their entireties.

RELATED APPLICATIONS

The present application claims priority under 35 U.S.C. §119(e) to U.S. provisional patent applications, U.S. Ser. No. 60/811,961, filed Jun. 8, 2006; and U.S. Ser. No. 60/909,780, filed Apr. 3, 2007; each of which is incorporated herein by reference.

BACKGROUND OF THE INVENTION

Inhibitors of histone deacetylase (HDAC) play an important role in the modulation of cellular proliferation. There are a wide variety of pathological cell proliferative conditions for which HDAC inhibitor therapeutics may be used. For instance, HDAC inhibitors have been found to be useful in the treatment of cancer, and particularly in the treatment of hematological and lymphoid malignancies. HDAC inhibitors have also been found to be useful in the treatment of immune-mediated disorders, conditions, and diseases (e.g., transplant rejection, graft-versus-host disease, immune reaction to gene therapy, autoimmune diseases, traumatic or pathogen induced immune dysregulation, inflammatory diseases, etc.), as well as in the treatment of cardiovascular diseases. In addition, HDAC inhibitors have been found to be useful in the treatment of a variety of neurodegenerative diseases. Furthermore, HDAC inhibitors have been implicated in chromatin remodeling.

Given the great potential of HDAC inhibitors as therapeutic agents in the treatment of a variety of diseases, there is a need to develop improved systems for the administration of HDAC inhibitors, and particularly for administrations that minimize potential side effects.

SUMMARY OF THE INVENTION

The present invention encompasses the finding that individuals with low potassium and/or magnesium levels are susceptible to development of unwanted side effects if administered deacetylase ("DAC"; e.g., HDAC, TDAC) inhibitor therapy.

The present invention provides methods of administering DAC inhibitor therapy comprising assessing electrolyte (e.g., potassium and/or magnesium) levels in an individual to whom therapy is to be administered, and optionally administering electrolyte (e.g., potassium and/or magnesium) supplementation prior to administration of DAC inhibitor therapy.

The present invention further provides methods of administering DAC inhibitor therapy comprising assessing electrolyte (e.g., potassium and/or magnesium) levels in an individual receiving one or more DAC inhibitors (whether alone or in combination with one or more other therapeutic agents, including other chemotherapeutic agents), and optionally administering electrolyte (e.g., potassium and/or magnesium) supplementation during DAC inhibitor therapy.

Specifically, the present invention demonstrates that electrolyte supplementation prior to, concurrently, and/or sequentially with DAC inhibitor treatment mitigates certain side effects that can be associated with such treatment. This observation indicates that electrolyte supplementation can be used in combination with DAC inhibitor treatment. In some embodiments, such treatment is of cell proliferative diseases (e.g., cancer or benign neoplasms).

To give but a few examples, in some embodiments, such treatment is of leukemias (e.g., chronic lymphocytic leukemia (CLL), chronic myelogenous leukemia (CML), acute lymphocytic leukemia (ALL), acute myelogenous leukemia (AML), adult T cell leukemia/lymphoma, etc.), lymphomas (e.g., Hodgkin's or non-Hodgkin's [e.g., T-cell lymphomas such as peripheral T-cell lymphomas (PTCL), cutaneous T-cell lymphomas (CTCL), etc.]), multiple myeloma, and/or myelodysplastic syndromes. Alternatively or additionally, in some embodiments, such treatment is of solid tumors such as lung, breast, colon, liver, pancreas, ovarian, prostate, kidney, sarcoma, and/or brain. In some embodiments, such treatment is of immune-mediated disorders such as graft vs. host disease, rheumatoid arthritis, systemic lupus erythematosus, psoriasis, atopic dermatitis, Crohn's disease, ulcerative colitis, and/or multiple sclerosis. In some embodiments, such treatment is of neurodegenerative diseases such as Alzheimer's disease, Parkinson's disease, and/or Huntington's disease. In some embodiments, the treatment is to enhance gene therapy.

The invention therefore provides, among other things, methods of treating DAC-mediated disorders, diseases, and/or conditions, including HDAC-mediated disorders, diseases, and/or conditions, such as cancers or proliferative diseases, comprising administering an electrolyte supplementation prior to, concurrently, and/or or sequentially with administration of a therapeutically effective amount of at least one deacetylase (e.g., HDAC) inhibitor.

The invention also provides methods of using a DAC inhibitor in the manufacture of a medicament to treat DAC-mediated diseases including HDAC-mediated diseases, such as cancers or other proliferative diseases in a patient that has received and/or is receiving electrolyte supplementation.

DEFINITIONS

Alicyclic: The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

Aliphatic: An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Aryl: The term "aryl," as used herein, refers to a mono- or polycyclic carbocyclic ring system having one or two aromatic rings including, but not limited to, phenyl, naphthyl, tetrahydronaphthyl, indanyl, idenyl and the like. In accordance with the invention, any of the aryls, substituted aryls, heteroaryls and substituted heteroaryls described herein, can be any aromatic group. Aromatic groups can be substituted or unsubstituted.

Cell Proliferative Disorder, Disease, or Condition: The term "cell proliferative disease or condition" is meant to refer to any condition characterized by aberrant cell growth, preferably abnormally increased cellular proliferation.

Electrolyte: In general, the term "electrolyte", as used herein, refers to physiologically relevant free ions. Representative such free ions include, but are not limited to sodium ($Na^+$), potassium ($K^+$), calcium ($Ca^{2+}$), magnesium ($Mg^{2+}$), chloride ($Cl^-$, phosphate ($PO_4^{3-}$), and bicarbonate ($HCO_3^-$).

DAC Inhibitor: In general, any agent that specifically inhibits a deacetylase is considered to be a DAC inhibitor. Any agent that specifically inhibits a histone deacetylase is considered to be an HDAC inhibitor. Any agent that specifically inhibits a tubulin deacetylase is considered to be a TDAC inhibitor. Those of ordinary skill in the art will appreciate that, unless otherwise set forth herein or known in the art, DAC inhibitors may be administered in any form such as, for example, salts, esters, prodrugs, etc. Furthermore, DAC inhibitors that contain chiral centers may be administered as single stereoisomers or as mixtures, including racemic mixtures, so long as the single stereoisomer or mixture has DAC inhibitor activity.

DAC Inhibitor Therapy: As used herein, the phrase "DAC inhibitor therapy" refers to the regimen by which a DAC inhibitor is administered to an individual. A DAC inhibitor may be administered alone or in combination with another pharmaceutical agent. In certain embodiments, a synergistic combination of a DAC inhibitor and another agent are administered. In certain embodiments, a DAC inhibitor is combined with a cytotoxic agent approved for use in treating cancer. For example, a combination of romidepsin and a proteasome inhibitor (e.g., bortezomib (VELCADE™)) may be administered. In but another example, a combination of romidepsin and gemcitabine is administered. In certain embodiments, romidepsin is combined with a taxane. In certain embodiments, romidepsin is combined with a topoisomerase inhibitor. In certain embodiments, romidepsin is combined with an anti-metabolite (e.g., 5-fluorouracil). In certain embodiments, romidepsin is combined with a tyrosine kinase inhibitor (e.g., Tarceva). In certain embodiments, romidepsin is combined with a DNA-crosslinking agent (e.g., cis-platin). In certain embodiments, romidepsin is combined with an anthracycline. Commonly, DAC inhibitor therapy will involve administration of multiple individual doses of a DAC inhibitor, spaced out over time. Such individual doses may be of different amounts or of the same amount. Furthermore, those of ordinary skill in the art will readily appreciate that different dosing regimens (e.g., number of doses, amount(s) of doses, spacing of doses) are typically employed with different DAC inhibitors. Those of ordinary skill in the art will also appreciate that, when a DAC inhibitor is administered in combination with one or more other agents, individual doses of the DAC inhibitor and the other agent(s) may be administered at the same time or at different times. For purposes of the present invention, when electrolyte supplementation is administered "prior to, during, or after" DAC inhibitor therapy, it may be administered prior to initiation of DAC inhibitor therapy (i.e., prior to administration of any dose) or prior to, concurrently with, or after any particular dose or doses.

Halogen: The term "halogen," as used herein, refers to an atom selected from fluorine, chlorine, bromine, and iodine.

Heteroaryl: The term "heteroaryl," as used herein, refers to a mono- or polycyclic (e.g., bi-, or tri-cyclic or more) aromatic radical or ring having from five to ten ring atoms of which one or more ring atom is selected from, for example, S, O, and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

Heterocyclic: The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

Initiation: As used herein, the term "initiation" when applied to therapy can refer to a first administration of a DAC (e.g., HDAC) inhibitor to a patient who has not previously received a DAC inhibitor. Alternatively or additionally, the term "initiation" can refer to administration of a particular dose of a DAC (e.g., HDAC) inhibitor during therapy of a patient.

Pharmaceutically acceptable carrier or excipient: As used herein, the term "pharmaceutically acceptable carrier or excipient" means a non-toxic, inert solid, semi-solid or liquid filler, diluent, encapsulating material or formulation auxiliary of any type.

Pharmaceutically acceptable ester: As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutically acceptable prodrug: The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews*, 8:1-38(1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Pharmaceutically acceptable salt: As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Romidepsin: The term "romidepsin" refers to a natural product of the chemical structure:

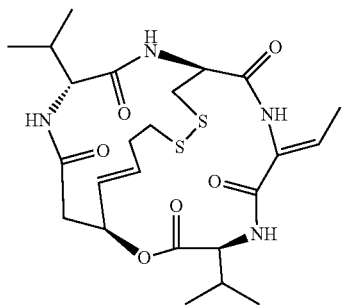

Romidepsin is a potent HDAC inhibitor and is also known in the art by the names FK228, FR901228, NSC630176, or depsipeptide. The identification and preparation of romidepsin is described in U.S. Pat. No. 4,977,138, which is incorporated herein by reference. The molecular formula is $C_{24}H_{36}N_4O_6S_2$; and the molecular weight is 540.71. Romidepsin has the chemical name, (1S,4S,10S,16E,21R)-7-[(2Z)-ethylidene]-4,21-diisopropyl-2-oxa-12,13-dithia-5,8,20,23-tetraazabicyclo[8.7.6]tricos-16-ene-3,6,9,19,22-pentanone. Romidepsin has been assigned the CAS number 128517-07-7. In crystalline form, romidepsin is typically a white to pale yellowish white crystal or crystalline powder. The term "romidepsin" encompasses this compound and any pharmaceutically acceptable salt forms thereof. In certain embodiments, the term "romidepsin" may also include prodrugs, esters, protected forms, and derivatives thereof.

Stable: The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). In general, combinations of substituents and variables envisioned by this invention are only those that result in the formation of stable compounds.

Substituted: The terms "substituted aryl", "substituted heteroaryl, or "substituted aliphatic," as used herein, refer to aryl, heteroaryl, aliphatic groups as previously defined, substituted by independent replacement of one, two, or three or more of the hydrogen atoms thereon with substituents including, but not limited to, —F, —Cl, —Br, —I, —OH, protected hydroxyl, —$NO_2$, —CN, —$C_1$-$C_{12}$-alkyl optionally substituted with, for example, halogen, $C_2$-$C_{12}$-alkenyl optionally substituted with, for example, halogen, —$C_2$-$C_{12}$-alkynyl optionally substituted with, for example, halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC (NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

Susceptible to: The term "susceptible to", as used herein refers to an individual having higher risk (typically based on genetic predisposition, environmental factors, personal history, or combinations thereof) of developing a particular disease or disorder, or symptoms thereof, than is observed in the general population.

Therapeutically effective amount: The term "therapeutically effective amount" of an active agent or combination of agents is intended to refer to an amount of agent(s) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of a particular agent may range from about 0.1 mg/Kg to about 500 mg/Kg, preferably from about 1 to about 50 mg/Kg. Effective doses may also vary depending on route of administration, as well as the possibility of co-usage with other agents. It will be understood, however, that the total daily usage of any particular active agent utilized in accordance with the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

Therapeutic agent: As used herein, the phrase "therapeutic agent" refers to any agent that, when administered to a subject, has a therapeutic effect and/or elicits a desired biological and/or pharmacological effect.

Treatment: As used herein, the term "treatment" (also "treat" or "treating") refers to any administration of a biologically active agent that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF CERTAIN EMBODIMENTS OF THE INVENTION

As indicated, the present invention provides methods and compositions relating to treatment of cell proliferation diseases in a patient in need thereof. The present invention also provides methods and compositions relating to treatment of individuals with DAC inhibitors, including HDAC inhibitors. In particular, the present invention provides methods and compositions that involve assessing one or more electrolyte (e.g., potassium and/or magnesium) levels in an individual receiving or scheduled to receive DAC inhibitor therapy, and/or administering to the individual electrolyte supplementation prior to, concurrently with and/or sequentially with at least one deacetylase inhibitor (e.g., at least one HDAC inhibitor). The DAC inhibitor may be administered alone or in combination with one or more other therapeutic agents, including one or more other chemotherapeutic agents.

Cell Proliferative Disorders, Diseases, or Conditions

In some embodiments, the invention provides methods for treating cell proliferative disorders, diseases or conditions. In general, cell proliferative disorders, diseases or conditions encompass a variety of conditions characterized by aberrant cell growth, preferably abnormally increased cellular proliferation. For example, cell proliferative disorders, diseases, or conditions include, but are not limited to, cancer, immune-mediated responses and diseases (e.g., transplant rejection, graft vs host disease, immune reaction to gene therapy, autoimmune diseases, pathogen-induced immune dysregulation, etc.), certain circulatory diseases, and certain neurodegenerative diseases.

In certain embodiments, the invention relates to methods of treating cancer. In general, cancer is a group of diseases which are characterized by uncontrolled growth and spread of abnormal cells. Examples of such diseases are carcinomas, sarcomas, leukemias, lymphomas and the like. In certain embodiments, the cancer is a hematological malignancy. In certain embodiments, the cancer is a solid tumor.

For example, cancers include, but are not limited to leukemias and lymphomas such as cutaneous T-cell lymphomas (CTCL), peripheral T-cell lymphomas, lymphomas associated with human T-cell lymphotropic virus (HTLV) such as adult T-cell leukemia/lymphoma (ATLL), B-cell lymphoma, acute lymphocytic leukemia, acute nonlymphocytic leukemias, chronic lymphocytic leukemia, chronic myelogenous leukemia, acute myelogenous leukemia, Hodgkin's disease, non-Hodgkin's lymphomas, multiple myeloma, myelodysplastic syndrome, mesothelioma, common solid tumors of adults such as head and neck cancers (e.g., oral, laryngeal and esophageal), genitourinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer, and/or childhood solid tumors such as brain tumors, neuroblastoma, retinoblastoma, Wilms' tumor, bone tumors, and soft-tissue sarcomas.

In some embodiments, the invention relates to treatment of leukemias. For example, in some embodiments, the invention relates to treatment of chronic lymphocytic leukemia, chronic myelogenous leukemia, acute lymphocytic leukemia, acute myelogenous leukemia, and/or adult T cell leukemia/lymphoma. In certain embodiments, the invention relates to the treatment of AML. In certain embodiments, the invention relates to the treatment of ALL. In certain embodiments, the invention relates to the treatment of CML. In certain embodiments, the invention relates to the treatment of CLL.

In some embodiments, the invention relates to treatment of lymphomas. For example, in some embodiments, the invention relates to treatment of Hodgkin's or non-Hodgkin's (e.g., T-cell lymphomas such as peripheral T-cell lymphomas, cutaneous T-cell lymphomas, etc.) lymphoma.

In some embodiments, the invention relates to the treatment of multiple myeloma and/or myelodysplastic syndromes. In some embodiments, the invention relates to treatment of solid tumors. In some such embodiments the invention relates to treatment of solid tumors such as lung, breast, colon, liver, pancreas, renal, prostate, ovarian, and/or brain. In some embodiments, the invention relates to treatment of pancreatic cancer. In some embodiments, the invention relates to treatment of renal cancer. In some embodiments, the invention relates to treatment of prostate cancer. In some embodiments, the invention relates to treatment of sarcomas. In some embodiments, the invention relates to treatment of soft tissue sarcomas. In some embodiments, the invention relates to methods of treating one or more immune-mediated responses and diseases.

For example, in some embodiments, the invention relates to treatment of rejection following transplantation of synthetic or organic grafting materials, cells, organs, or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; treatment of graft-versus-host disease; autoimmune diseases, such as rheumatoid arthritis, systemic lupus erythematosus, thyroiditis, Hashimoto's thyroiditis, multiple sclerosis, myasthenia gravis, type I diabetes, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treatment of infectious diseases causing aberrant immune response and/or activation, such as traumatic or pathogen induced immune dysregulation, including for example, that which are caused by hepatitis B and C infections, HIV, *Staphylococcus aureus* infection, viral encephalitis, sepsis, parasitic diseases wherein damage is induced by an inflammatory response (e.g., leprosy). In some embodiments, the invention relates to treatment of graft vs host disease, rheumatoid arthritis, systemic lupus erythematosus, psoriasis, atopic dermatitis, Crohn's disease, ulcerative colitis, and/or multiple sclerosis.

Alternatively or additionally, in some embodiments, the invention relates to treatment of an immune response associated with a gene therapy treatment, such as the introduction of foreign genes into autologous cells and expression of the encoded product. In some embodiments, the invention relates to treatment of circulatory diseases, such as arteriosclerosis, atherosclerosis, vasculitis, polyarteritis nodosa and/or myocarditis.

In some embodiments, the invention relates to treatment of any of a variety of neurodegenerative diseases, a non-exhaustive list of which includes:

I. Disorders characterized by progressive dementia in the absence of other prominent neurologic signs, such as Alzheimer's disease; Senile dementia of the Alzheimer type; and Pick's disease (lobar atrophy);

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy);

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome;

IV. Syndromes of progressive ataxia such as cerebellar degenerations (e.g., cerebellar cortical degeneration and olivopontocerebellar atrophy (OPCA)); and spinocerebellar degeneration (Friedreich's ataxia and related disorders);

V. Syndromes of central autonomic nervous system failure (Shy-Drager syndrome);

VI. Syndromes of muscular weakness and wasting without sensory changes (motomeuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia;

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy;

VIII. Syndromes of progressive visual loss such as pigmentary degeneration of the retina (retinitis pigmentosa), and hereditary optic atrophy (Leber's disease).

In some embodiments, the neurodegenerative disease is Alzheimer's disease, Parkinson's disease, and/or Huntington's disease.

In some embodiments, the invention relates to treatment of disorders, diseases or conditions associated with chromatin remodeling.

Electrolyte Supplementation

The present invention encompasses the finding that individuals with low electrolyte levels (e.g., low potassium and/or magnesium levels) are susceptible to development of unwanted side effects if administered DAC inhibitor therapy (e.g., HDAC inhibitor therapy). Specifically, according to the present invention, such patients may be particularly susceptible to development of cardiac repolarization effects, including QTc prolongation (though potentially with no significant cardiac function changes), and/or cardiac dysrhythmias. Particular abnormalities that may be observed include an increase in QTc interval and/or abnormalities of the ST segment (e.g., ST segment depression) and/or the T-wave (e.g., T-wave flattening).

According to the present invention, an individual with a potassium serum concentration below about 3.5 mmol/L (3.5 mEq/L) and/or a serum magnesium concentration below about 0.8 mml/L (1.95 mEq/L) suffers an increased risk of developing cardiac repolarization effects and/or dysrhythmias.

Serum concentrations of potassium are generally considered to be "normal" when they are within the range of about 3.5-5.5 mEq/L or about 3.5-5.0 mEq/L. According to the present invention, it is often desirable to ensure that an individuals' serum potassium concentration is within these ranges prior to (and/or during) administration of DAC inhibitor therapy.

Serum concentrations of magnesium are generally considered to be "normal" when they are within the range of about 1.5-2.5 mEq/L or about 1.5-2.2 mEq/L or about 1.25-2.5 mEq/L or about 1.25-2.2 mEq/L. According to the present invention, it is often desirable to ensure that an individual's serum magnesium concentration is within these ranges prior to (and/or during) administration of DAC inhibitor therapy.

In some embodiments of the invention, an individual's serum potassium and/or magnesium concentration(s) is/are at the high end of the normal range prior to (and/or during) administration of DAC inhibitor therapy. For example, in some embodiments, an individual's serum potassium concentration is at least about 3.8 mEq/L, 3.9 mEq/L, 4.0 mEq/L, or more prior to and/or during administration of DAC inhibitor therapy. In some embodiments, care is taken not to increase serum potassium concentration above about 5.0 mEq/L, 5.2 mEq/L, or 5.5 mEq/L. In some embodiments, an individual's serum magnesium concentration is at least about 1.9 mEq/L or more prior to and/or during administration of DAC inhibitor therapy. In some embodiments, care is taken not to increase magnesium concentration above about 2.5 mEq/L.

In some embodiments of the present invention, an individual's serum potassium concentration is at least about 3.5 mEq/L (in some embodiments at least about 3.8 mEq/L, 3.9 mEq/L, 4.0 mEq/L, or above) and the individual's serum magnesium concentration is at least about 1.85 mEq/L (in some embodiments at least about 1.25 mEq/L, 1.35 mEq/L, 1.45 mEq/L, 1.55 mEq/L, 1.65 mEq/L, 1.75 mEq/L, 1.85 mEq/L, 1.95 mEq/L, or above) prior to and/or during administration of DAC inhibitor therapy.

In some embodiments of the invention, electrolyte levels (e.g., potassium and/or magnesium levels, optionally calcium levels) are assessed more than once during the course of DAC inhibitor therapy; in some embodiments, different assessments are separated by a regular interval (e.g., 0.5 days or less, 1 day, 2 days, 3 days, 4 days, 5 days, 6 days, 7 days, 8 days, 9 days, 10 days, 11 days, 12 days, 13 days, 14 days, 1 month, 2 months, 3 months, 4 months, 5 months, 6 months, etc.). In some embodiments, electrolyte levels are assessed prior to each administration of DAC inhibitor.

According to the present invention, an individual's serum potassium and/or magnesium and/or other electrolyte concentration(s) may be assessed by any available means. For example, samples may be collected from venous or arterial blood and processed for plasma or serum analysis. In some embodiments, venous sampling is utilized. Any available assay may be utilized for assessment. To give but a few specific examples, potassium may be measured by flame photometry, direct potentiometry (see, for example, Koch et al., *Clin. Chem.* 29:1090, 1983), enzymatic methods (e.g., by using tryptophanase, see, for example, Kimura et al., *Clin. Chem.* 38:44, 1992), colorimetric methods (e.g., using tetraphenyl borate), etc.; magnesium may be measured by complexometric titration, flame emission photometry, atomic absorption spectophotometry, other spectrophotometric techniques including enzymatic techniques and dye binding methods (e.g., Magnon dye binding and bichromatic absorbance, see, for example, Barbour et al., *Clin. Chem.* 34:2103, 1988; elimination of interference by bilirubin, see, for example, Rehak et al., *Clin. Chem* 35:1031, 1989; etc.). In many embodiments, assays are performed in an automated clinical chemistry analyzer (e.g., the Abbott ARCHITECT®, etc.)

Where both potassium and magnesium levels are assessed, they may be assessed separately or together. Assessment of potassium and/or magnesium levels may be performed prior to, at the same time as, and/or after initiation of DAC inhibitor therapy.

If an individual is determined to have serum potassium and/or magnesium concentration(s) that is/are below normal, or below the high end of normal as described herein, according to the present invention, potassium and/or magnesium supplementation is administered prior to, at the same time as, or after initiation of DAC inhibitor therapy. In some embodiments, DAC inhibitor therapy is suspended or delayed until serum potassium and/or magnesium levels are increased. In some embodiments, DAC inhibitor therapy is suspended or delayed until serum potassium and/or magnesium levels are increased to within the normal range, or to within the upper end of the normal range. In some embodiments, DAC inhibitor therapy is suspended or delayed until serum potassium concentration is above about 3.5 mEq/L; in some embodiments until serum potassium concentration is above about 3.8 mEq/L. In some embodiments, DAC inhibitor therapy is suspended or delayed until serum magnesium concentration is above about 1.25 mEq/L; in some embodiments until serum magnesium concentration is above about 1.8 mEq/L; in some embodiments until serum magnesium concentration is above about 1.9 mEq/L. In some embodiments, DAC inhibitor therapy is suspended or delayed until both serum potassium and serum magnesium concentrations are increased as described herein.

According to the present invention, electrolyte supplementation, which may be administered prior to, concurrently with, and/or subsequent to initation of DAC inhibitor therapy, may include potassium and/or magnesium supplementation. Alternatively or additionally, electrolyte supplementation may include supplementation of one or more electrolytes selected from the group consisting of sodium, potassium, chloride, calcium, magnesium, bicarbonate, phosphate, sulfate, and combinations thereof.

A variety of different potassium supplemental forms are available (see, for example, www.pdrhealth.com). For example, potassium supplements in the form of potassium chloride, potassium citrate, potassium gluconate, potassium bicarbonate, potassium aspartate and/or potassium orotate can readily be obtained.

High-potassium (up to 800 milligrams per serving), low-sodium vegetable juices are available. Some soft drinks are rich in potassium. Some soft drinks contain, potassium gluconate which has a less bitter taste than some other potassium supplements. Salt substitutes are high in potassium.

Certain foods high in potassium such as raisins, figs, apricots, sardines, veal, bananas, avocado, and broccoli may be used as potassium supplements. Foods high in potassium may provide potassium that is easily bioavailable and/or may reduce gastrointestinal side effects associated with the administration of potassium salts. The potassium supplement may also be provided as part of a multivitamin.

Potassium is typically supplemented orally or intravenously, though other modes of delivery are within the scope of the present invention.

Certain commercially available forms of potassium supplements include, for example, potassium acetate (e.g., 2 mEq/mL or 4 mEq/mL for injection); potassium acetate (e.g., 75 mg, 95 mg, 99 mg, and 180 mg tablets and/or 2 mEq/mL, 10 mEq/50 mL, 20 mEq/50 mL, 10 mEq/100 mL, 20 mEq/100 mL, 30 mEq/100 mL, 40 mEq/100 mL for injection and/or 20 mEq/15 mL, 40 mEq/15 mL liquid and/or 20 mEq or 25 mEq powder for reconstitution, and/or 9 mEq, 10 mEq, or 20 mEq extended release tablets), and potassium gluconate (e.g., 486 mg, 500 mg, 550 mg, 595 mg, 610 mg, and 620 mg tablets).

A variety of different magnesium supplemental forms are also available. For example, supplements in the form of magnesium chloride, magnesium gluconate, magnesium lactate, magnesium oxide and/or magnesium sulfate can readily be obtained.

Certain foods high in magnesium such as artichoke, banana, figs, almonds, cashews, pine nuts, brazil nuts, beans, spinach, and tomatoes may be used as magnesium supplements. The magnesium supplement may also be provided as part of a multivitamin.

Certain commercially available forms of magnesium supplements include magnesium chloride (e.g., 200 mg/ml for injection, 535 mg extended release tablets), magnesium gluconate (3.25 mg/mL, 1000 mg/5 mL liquid; 500 mg tablet); magnesium lactate (84 mg extended release tablet); magnesium oxide (e.g., 140 mg, 600 mg capsules, powder, and/or 200 mg, 250 mg, 400 mg, 420 mg, and 500 mg tablets), magnesium sulfate (e.g., 40 mg/mL, 80 mg/mL, 125 mg/mL, 500 mg/mL for injection).

In some embodiments, electrolyte supplementation administered in accordance with the present invention treats one or more side effect(s) of DAC (e.g., HDAC) inhibitor therapy. For example, cardiac events have also been reported in clinical trials with DAC inhibitors. Specifically, ECG abnormalities, tachyarrhythmias, and QTc prolongation have been reported. ECG effects described as non-specific T-wave or ST segment abnormalities have been reported with the use of romidepsin (aka depsipeptide), SAHA and LAQ824 (13, 45-47). Supraventricular tachycardia, a dose-limiting event reported from the NCI phase I trial with romidepsin (aka depsipeptide), was reported as a dose limiting toxicity in a phase I trial of PXD101, and was reported in patients treated on a phase I trial of MS-275 when administered daily (13, 48, 49). In patients treated with LBH589, a hydroxamic acid, QTc prolongation of greater than 500 ms was noted in 5 of 12 (42%) patients treated at higher dose levels (50). QTc prolongation associated with LAQ824, another hydroxamic acid, was also reported (47). Of note, a statistically significant increase in QTc interval was reported, with 10% of 77 patients treated having QTc prolongation of greater than 60 ms. One patient found to have QTc greater than 500 ms experienced torsades de pointes when re-treated at a lower dose level (47).

In some embodiments of the present invention, electrolyte supplementation is administered sufficient to reduce or delay onset of one or more cardiac side effects of DAC (e.g., HDAC) inhibitor therapy. In some embodiments, the electrolyte administration may also reduce one or more of nausea, vomiting, fatigue (lethargy, malaise, asthenia), increased creatine phospho kinase (CPK), hyperuricemia, hypocalcemia, hyperglycemia, fever, gastritis, diarrhea, abdominal pain, dehydration, weight loss, hypophosphatemia, hyponatremia, hypokalemia, hypomagnesemia, syncope, hypoxia, pleural effusion, hypotension, myocardial ischemia, increased cardiac tropinin I, confusion, and/or myelosuppression, and combinations thereof.

In some embodiments, cardiac event side effects are selected from the group consisting of heart-rate corrected QT (QTc) interval prolongaion, supraventricular arrhythmias (supraventricular tachycardia (SVT)/atrial fibrillation/flutter), and combinations thereof. Specifically, in some embodiments, QTc prolongation and/or other electrophysiological changes are reduced to normal values or ranges DAC Inhibitors Deacetylase inhibitors, as that term is used herein are compounds which are capable of inhibiting the deacetylation of proteins in vivo, in vitro or both. In many embodiments, the invention relates to HDAC inhibitors, which inhibit the deacetylation of histones. However, those of ordinary skill in the art will appreciate that HDAC inhibitors often have a variety of biological activities, at least some of which may well be independent of histone deacetylase inhibition.

As indicated, DAC inhibitors inhibit the activity of at least one deacetylase. Where the DAC inhibitor is an HDAC inhibitor, an increase in acetylated histones occurs and accumulation of acetylated histones is a suitable biological marker for assessing the activity of HDAC inhibitors. Therefore, procedures which can assay for the accumulation of acetylated histones can be used to determine the HDAC inhibitory activity of agents of interest. Analogous assays can determine DAC inhibitory activity It is understood that agents which can inhibit deacetylase activity (e.g., histone deacetylase activity) typically can also bind to other substrates and as often can inhibit or otherwise regulate other biologically active molecules such as enzymes.

Suitable DAC or HDAC inhibitors according to the present invention include, for example, 1) hydroxamic acid derivatives; 2) Short-Chain Fatty Acids (SCFAs); 3) cyclic tetrapeptides; 4) benzamides; 5) electrophilic ketones; and/or any other class of compounds capable of inhibiting histone deacetylase. Examples of such DAC inhibitors include, but are not limited to:

A) HYDROXAMIC ACID DERIVATIVES such as Suberoylanilide Hydroxamic Acid (SAHA) (Richon et al., Proc. Natl. Acad. Sci. USA 95, 3003-3007 (1998)); M-Carboxycinnamic Acid Bishydroxamide (CBHA) (Richon et al., supra); pyroxamide; CBHA; Trichostatin analogues such as Trichostatin A (TSA) and Trichostatin C (Koghe et al. 1998. Biochem. Pharmacol. 56: 1359-1364); Salicylihydroxamic Acid (SBHA) (Andrews et al., International J. Parasitology 30, 761-768 (2000)); Azelaic Bishydroxamic Acid (ABHA) (Andrews et al., supra); Azelaic-1-Hydroxamate-9-Anilide (AAHA) (Qiu et al., Mol. Biol. Cell 11, 2069-2083 (2000)); 6-(3-Chlorophenylureido) carpoic Hydroxamic Acid (3Cl-UCHA), Oxamflatin [(2E)-5-[3-[(phenylsuibnyl-)amino phenyl]-pent-2-en-4-ynohydroxamic acid (Kim et al. Oncogene, 18: 2461 2470 (1999)); A-161906, Scriptaid (Su et al. 2000 Cancer Research, 60: 3137-3142); PXD-101 (Prolifix); LAQ-824; CHAP; MW2796 (Andrews et al., supra); and MW2996 (Andrews et al., supra).

B) CYCLIC TETRAPEPTIDES such as Trapoxin A (TPX)-Cyclic Tetrapeptide (cyclo-(L-phenylalanyl-L-phenylalanyl-D-pipecolinyl-L-2-amin-o-8-oxo-9,10-epoxy decanoyl)) (Kijima et al., J Biol. Chem. 268, 22429-22435 (1993)); FR901228 (FK 228, Depsipeptide, Romidepsin) (Nakajima et al., Ex. Cell Res. 241, 126-133 (1998)); FR225497 Cyclic Tetrapeptide (H. Mori et al., PCT Application WO 00/08048 (Feb. 17, 2000)); Apicidin Cyclic Tetrapeptide [cyclo(NO-methyl-L-tryptophanyl-L-isoleucinyl-D-pipe-colinyl-L-2-amino-8oxodecanoyl)] (Darkin-Rattray et al., Proc. Natl. Acad. Sci. USA 93, 1314313147 (1996)); Apicidin Ia, Apicidin Ib, Apicidin Ic, Apicidin IIa, and Apicidin IIb (P. Dulski a al., PCT Application WO 97/11366); CHAP, HC-Toxin Cyclic Tetrapeptide (Bosch et al., Plant Cell 7, 1941-1950 (1995)); WF27082 Cyclic Tetrapeptide (PCT Application WO 98/48825); and Chiamydocin (Bosch et al., supra).

C) SHORT CHAIN FATTY ACID (SCFA) DERIVATIVES such as: Sodium Butyrate (Cousens et al., J. Biol. Chem. 254, 1716-1723 (1979)); Isovalerate (McBain et al., Biochem. Pharm. 53: 1357-1368 (1997)); Valerate (McBain et al., supra); 4 Phenylbutyrate (4-PBA) (Lea and Tulsyan, Anticancer Research, 15, 879-873 (1995)); Phenylbutyrate (PB) (Wang et al., Cancer Research, 59, 2766-2799 (1999)); Propionate (McBain et al., supra); Butyramide (Lea and Tulsyan, supra); Isobutyramide (Lea and Tulsyan, supra); Phenylacetate (Lea and Tulsyan, supra); 3-Bromopropionate (Lea and Tulsyan, supra); Tributyrin (Guan et al., Cancer Research, 60, 749-755 (2000)); Valproic acid and Valproate.

D) BENZAMIDE DERIVATIVES such as CI-994; MS-275 [N-(2-aminophenyl)-4-[N-(pyridin-3-ylmethoxycarbonyl)aminomethyl]benzamid-e] (Saito et al., Proc. Natl. Acad. Sci. USA 96, 4592-4597 (1999)); and 3'-amino derivative of MS-27-275 (Saito et al., supra).

E) ELECTROPHILIC KETONE DERIVATIVES such as trifluoromethyl ketones (Frey et al, Bioorganic & Med. Chem. Lett. (2002), 12, 3443-3447; U.S. Pat. No. 6,511, 990) and α-keto amides such as N-methyl-α-ketoamides.

F) OTHER DAC Inhibitors such as Depudecin (Kwon et al. 1998. PNAS 95: 3356-3361).

In some embodiments, the DAC or HDAC inhibitor used in the method of the invention is represented by formula (I):

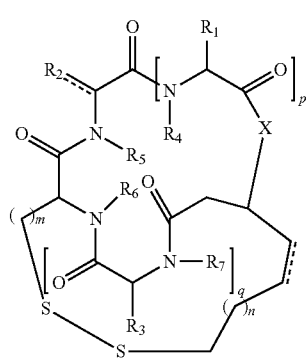

wherein
m is 1, 2, 3 or 4;
n is 0, 1, 2 or 3;
p and q are independently 1 or 2;
X is O, NH, or $NR_8$;
$R_1$, $R_2$, and $R_3$ are independently hydrogen; unsubstituted or substituted, branched or unbranched, cyclic or acyclic aliphatic; unsubstituted or substituted, branched or unbranched, cyclic or acyclic heteroaliphatic; unsubstituted or substituted aryl; or unsubstituted or substituted heteroaryl;
$R_4$, $R_5$, $R_6$, $R_7$ and $R_8$ are independently hydrogen; or substituted or unsubstituted, branched or unbranched, cyclic or acyclic aliphatic; and pharmaceutically acceptable forms thereof. In certain embodiments, m is 1. In certain embodiments, n is 1. In certain embodiments, p is 1. In certain embodiments, q is 1. In certain embodiments, X is O. In certain embodiments, $R_1$, $R_2$, and $R_3$ are unsubstituted, or substituted, branched or unbranched, acyclic aliphatic. In certain embodiments, $R_4$, $R_5$, $R_6$, and $R_7$ are all hydrogen.

In some embodiments, the DAC or HDAC inhibitor used in the method of the invention is represented by formula (II):

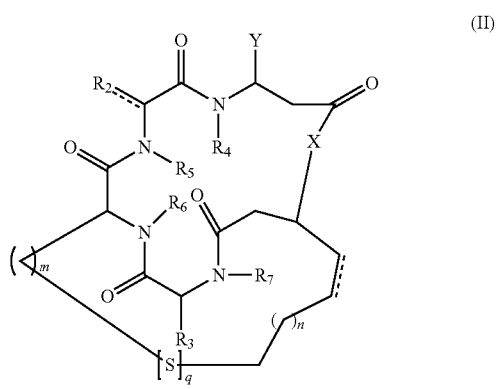

wherein:
m is 1, 2, 3 or 4;
n is 0, 1, 2 or 3;
q is 2 or 3;
X is O, NH, or $NR_8$;
Y is $OR_8$, or $SR_8$;
$R_2$ and $R_3$ are independently hydrogen; unsubstituted or substituted, branched or unbranched, cyclic or acyclic aliphatic; unsubstituted or substituted, branched or unbranched, cyclic or acylic heteroaliphatic; unsubstituted or substituted aryl; or unsubstituted or substituted heteroaryl;
$R_4$, $R_5$, $R_6$, $R_7$ and $R_8$ are independently selected from hydrogen; or substituted or unsubstituted, branched or unbranched, cyclic or acyclic aliphatic; and pharmaceutically acceptable forms thereof. In certain embodiments, m is 1. In certain embodiments, n is 1. In certain embodiments, q is 2. In certain embodiments, X is O. In other embodiments, X is NH. In certain embodiments, $R_2$ and $R_3$ are unsubstituted or substituted, branched or unbranched, acyclic aliphatic. In certain embodiments, $R_4$, $R_5$, $R_6$, and $R_7$ are all hydrogen.

In some embodiments, the DAC or HDAC inhibitor used in the method of the invention is represented by formula (III):

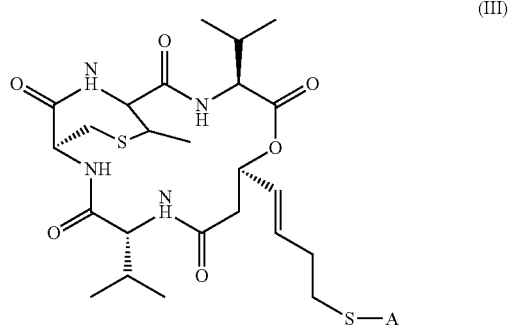

wherein
A is a moiety that is cleaved under physiological conditions to yield a thiol group and includes, for example, an aliphatic or aromatic acyl moiety (to form a thioester bond); an aliphatic or aromatic thioxy (to form a disulfide bond); or the like; and pharmaceutically acceptable forms thereof. Such aliphatic or aromatic groups can include a substituted or unsubstituted, branched or unbranched, cyclic or acyclic aliphatic group; a substituted or unsubstituted aromatic group; a substituted or unsubstituted heteroaromatic group; or a substituted or unsubstituted heterocyclic group. A can be, for example, —$COR_1$, —$SC(=)$—O—$R_1$, or —$SR_2$. $R_1$ is independently hydrogen; substituted or unsubstituted amino; substituted or unsubstituted, branched or unbranched, cyclic or acyclic aliphatic; substituted or unsubstituted aromatic group; substituted or unsubstituted heteroaromatic group; or a substituted or unsubstituted heterocyclic group. In certain embodiment, $R_1$ is hydrogen, methyl, ethyl, n-propyl, isopropyl, n-butyl, isobutyl, benzyl, or bromobenzyl. $R_2$ is a substituted or unsubstituted, branched or unbranched, cyclic or acyclic aliphatic group; a substituted or unsubstituted aromatic group; a substituted or unsubstituted heteroaromatic group; or a substituted or unsubstituted heterocyclic group. In certain embodiments, $R_2$ is methyl, ethyl, 2-hydroxyethyl, isobutyl, fatty acids, a substituted or unsubstituted benzyl, a substituted or unsubstituted aryl, cysteine, homocysteine, or glutathione.

In some embodiments, the DAC or HDAC inhibitor used in the method of the invention is represented by formula (IV) or (IV'):

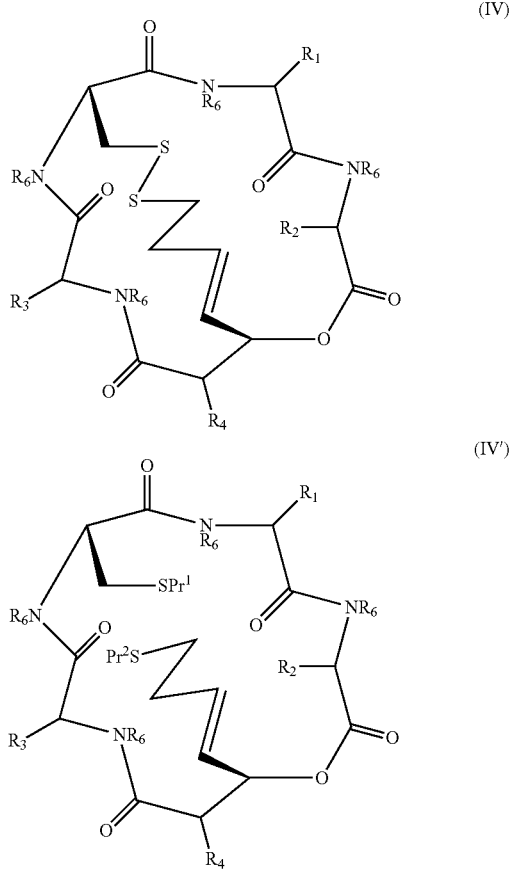

wherein $R_1$, $R_2$, $R_3$, and $R_4$ are the same or different and represent an amino acid side chain moiety, each $R_6$ is the same or different and represents hydrogen or $C_1$-$C_4$ alkyl, and $Pr^1$ and $Pr^2$ are the same or different and represent hydrogen or thiol-protecting group. In certain embodiments, the amino acid side chain moieties are those derived from natural amino acids. In other embodiments, the amino acid side chain moieties are those derived from unnatural amino acids. In certain embodiments, each amino acid side chain is a moiety selected from —H, —$C_1$-$C_6$ alkyl, —$C_2$-$C_6$ alkenyl, -L-O—C(O)—R', -L-C(O)—O—R", -L-A, -L-NR"R", -L-Het-C(O)-Het-R", and -L-Het-R", wherein L is a $C_1$-$C_6$ alkylene group, A is phenyl or a 5- or 6-membered heteroaryl group, each R' is the same or different and represents $C_1$-$C_4$ alkyl, each R" is the same or different and represent H or $C_1$-$C_6$ alkyl, each -Het- is the same or different and is a heteroatom spacer selected from —O—, —N(R''')—, and —S—, and each R''' is the same of different and represents H or $C_1$-$C_4$ alkyl. In certain embodiments, $R_6$ is —H. In certain embodiments, $Pr^1$ and $Pr^2$ are the same or different and are selected from hydrogen and a protecting group selected from a benzyl group which is optionally substituted by $C_1$-$C_6$ alkoxy, $C_1$-$C_6$ acyloxy, hydroxy, nitro, picolyl, picolyl-N-oxide, anthrylmethyl, diphenylmethyl, phenyl, t-butyl, adamanthyl, $C_1$-$C_6$ acyloxymethyl, $C_1$-$C_6$ alkoxymethyl, tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl, and $C_1$-$C_6$ alkylcarbamoyl. In certain embodiments, $Pr^1$ and $Pr^2$ are hydrogen. Various romidepsin derivatives of formula (IV) and (IV') are disclosed in published PCT application WO 2006/129105, published Dec. 7, 2006; which is incorporated herein by reference.

In some embodiments, the DAC or HDAC inhibitor used in the method of the invention is represented by formula (V):

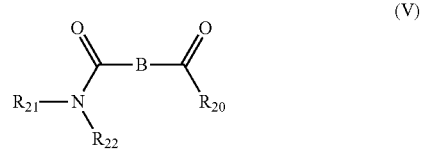

wherein

B is a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group; $R_{20}$ is hydroxylamino, hydroxyl, amino, alkylamino, dialkylamino, or alkyloxy group; $R_{21}$ and $R_{22}$ are independently selected from hydrogen, hydroxyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group. In a particular embodiment of Formula IV, $R_{20}$ is a hydroxylamino, hydroxyl, amino, methylamino, dimethylamino or methyloxy group and B is a $C_6$-alkyl. In yet another embodiment of Formula IV, $R_{21}$ is a hydrogen atom, $R_{22}$ is a substituted or unsubstituted phenyl and B is a $C_6$-alkyl. In further embodiments of Formula IV, $R_{21}$ is hydrogen and $R_{22}$ is an α-, β-, or γ-pyridine.

Other examples of DAC or HDAC inhibitors can be found in, for example, U.S. Pat. No. 5,369,108, issued on Nov. 29, 1994, U.S. Pat. No. 5,700,811, issued on Dec. 23, 1997, U.S. Pat. No. 5,773,474, issued on Jun. 30, 1998, U.S. Pat. No. 5,932,616 issued on Aug. 3, 1999 and U.S. Pat. No. 6,511, 990, issued Jan. 28, 2003 all to Breslow et al.; U.S. Pat. No.

5,055,608, issued on Oct. 8, 1991, U.S. Pat. No. 5,175,191, issued on Dec. 29, 1992 and U.S. Pat. No. 5,608,108, issued on Mar. 4, 1997 all to Marks et al.; U.S. Provisional Application No. 60/459,826, filed Apr. 1, 2003 in the name of Breslow et al.; as well as, Yoshida, M., et al., Bioassays 17, 423-430 (1995); Saito, A., et al., PNAS USA 96, 4592-4597, (1999); Furamai R. et al., PNAS USA 98 (1), 87-92 (2001); Komatsu, Y., et al., Cancer Res. 61(11), 4459-4466 (2001); Su, G. H., et al., Cancer Res. 60, 3137-3142 (2000); Lee, B. I. et al., Cancer Res. 61(3), 931-934; Suzuki, T., et al., J. Med. Chem. 42(15), 3001-3003 (1999); published PCT Application WO 01/18171 published on Mar. 15, 2001 Sloan-Kettering Institute for Cancer Research and The Trustees of Columbia University; published PCT Application WO02/246144 to Hoffmann-La Roche; published PCT Application WO02/22577 to Novartis; published PCT Application WO02/30879 to Prolifix; published PCT Applications WO 01/38322 (published May 31, 2001), WO 01/70675 (published on Sep. 27, 2001) and WO 00/71703 (published on Nov. 30, 2000) all to Methylgene, Inc.; published PCT Application WO 00/21979 published on Oct. 8, 1999 to Fujisawa Pharmaceutical Co., Ltd.; published PCT Application WO 98/40080 published on Mar. 11, 1998 to Beacon Laboratories, L.L.C.; and Curtin M. (Current patent status of histone deacetylase inhibitors Expert Opin. Ther. Patents (2002) 12(9): 1375-1384 and references cited therein).

Specific non-limiting examples of DAC or HDAC inhibitors are provided in the Table below. It should be noted that the present invention encompasses any compounds which both are structurally similar to the compounds represented below and are capable of inhibiting histone deacetylases.

| Title | |
|---|---|
| MS-275 | 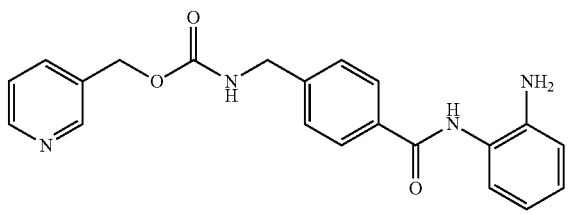 [SMILES: Nc1ccccc1NC(=O)c1ccc(CNC(=O)OCc2cccnc2)cc1] |
| DEPSIPEPTIDE | 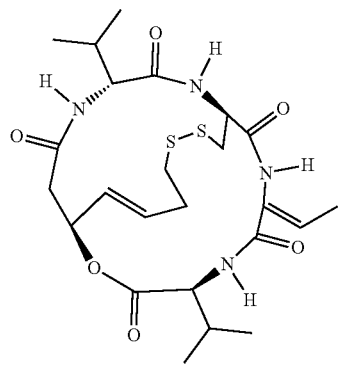 [SMILES: C/C=C1\NC(=O)[C@H]2CSSCC/C=C/[C@H](CC(=O)N[C@H](C(C)C)C(=O)N2)OC(=O)[C@H](C(C)C)NC1=O] |
| CI-994 | 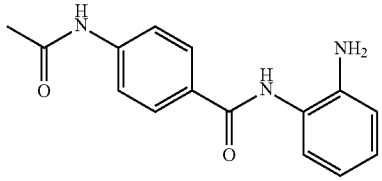 [SMILES: CC(=O)Nc1ccc(C(=O)Nc2ccccc2N)cc1] |
| Apicidin | 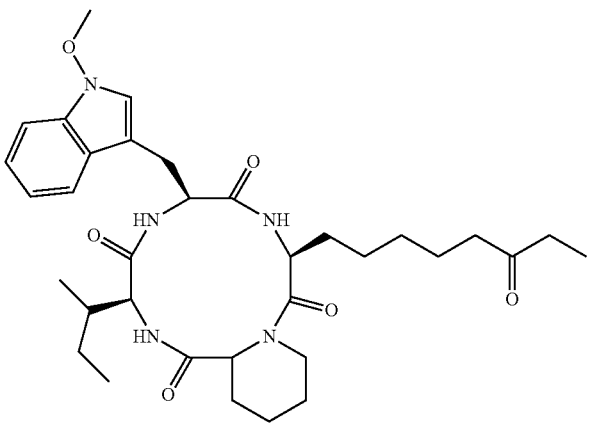 [SMILES: CCC(=O)CCCCC[C@@H]1NC(=O)[C@H](Cc2cn(OC)c3ccccc23)NC(=O)[C@H](C(C)CC)NC(=O)C2CCCCN2C1=O] |

-continued
| Title | |
|---|---|
| A-161906 | 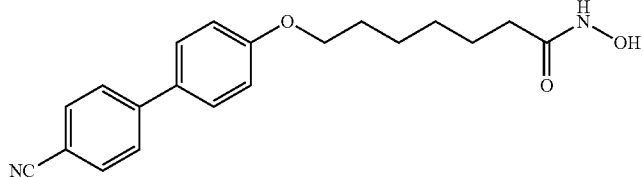 [SMILES: N#Cc1ccc(-c2ccc(OCCCCCCC(=O)NO)cc2)cc1] |
| Scriptaid | 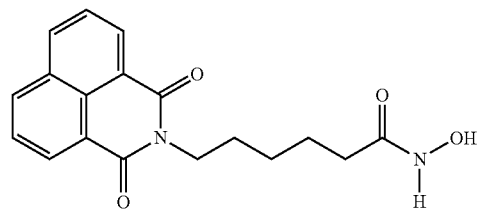 [SMILES: O=C(CCCCCN1C(=O)c2cccc3cccc(c23)C1=O)NO] |
| PXD-101 | 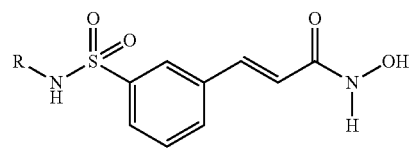 |
| CHAP | 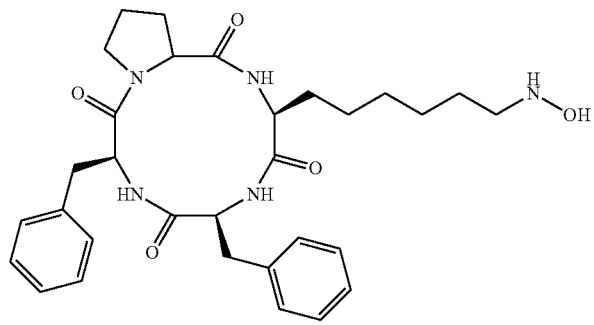 [SMILES: O=C1N[C@@H](CCCCCCNO)C(=O)N[C@@H](Cc2ccccc2)C(=O)N[C@@H](Cc2ccccc2)C(=O)N2CCCC12] |
| LAQ-824 | 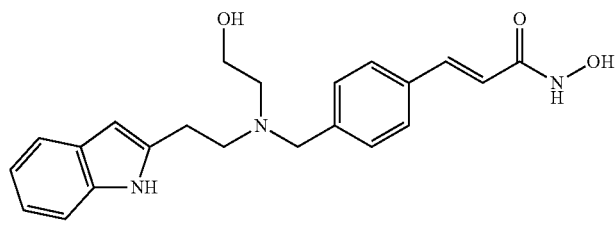 [SMILES: O=C(/C=C/c1ccc(CN(CCO)CCc2cc3ccccc3[nH]2)cc1)NO] |
| Butyric Acid | 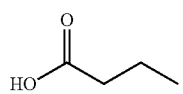 |
| Depudecin | 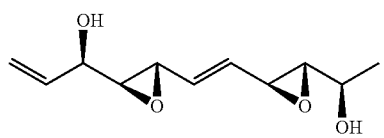 |

-continued

| Title | |
|---|---|
| Oxamflatin | 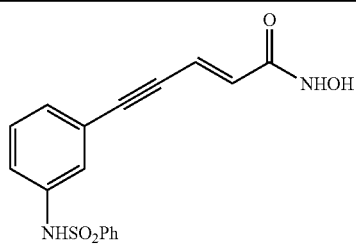 |
| Trichostatin C | 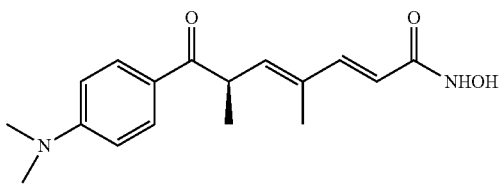 |

DAC or HDAC inhibitors for use in accordance with the present invention may be prepared by any available means including, for example, synthesis, semi-synthesis, or isolation from a natural source.

DAC or HDAC inhibitors for use in accordance with the present invention may be isolated or purified. For example, synthesized compounds can be separated from a reaction mixture, and natural products can be separated from their natural source, by methods such as column chromatography, high pressure liquid chromatography, and/or recrystallization.

A variety of synthetic methodologies for preparing DAC or HDAC inhibitors are known in the art. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

DAC or HDAC inhibitors for use in accordance with the present invention may be modified as compared with presently known DAC or HDAC inhibitors, for example, by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

In some embodiments, a DAC (e.g., HDAC) inhibitor for use in accordance with the present invention may contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention encompasses all such possible isomers, as well as their racemic and optically pure forms to the extent that they have DAC inhibitory activity.

In general, optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

In some embodiments, a DAC (e.g., HDAC) inhibitor for use in accordance with the present invention may contain olefinic double bonds, other unsaturation, or other centers of geometric asymmetry. The present invention encompasses both E and Z geometric isomers or cis- and trans-isomers to the extent that they have DAC inhibitory activity. The present invention likewise encompasses all tautomeric forms that have DAC inhibitory activity. In general, where a chemical structure is presented, the configuration of any carbon-carbon double bond appearing herein is selected for convenience only and is not intended to designate a particular configuration unless the text so states or it is otherwise clear from context; thus a carbon-carbon double bond or carbon-heteroatom double bond depicted arbitrarily herein as trans may be cis, trans, or a mixture of the two in any proportion.

DAC inhibitors (e.g., HDAC inhibitors) are particularly useful in the treatment of neoplasms in vivo. However, they may also be used in vitro for research or clinical purposes (e.g., determining the susceptibility of a patient's disease to a particular DAC inhibitor). In certain embodiments, the neoplasm is a benign neoplasm. In other embodiments, the neoplasm is a malignant neoplasm. Any cancer may be treated using a DAC inhibitor alone or in combination with another pharmaceutical agent.

In certain, embodiments, the malignancy is a hematological malignancy. Manifestations can include circulating malignant cells as well as malignant masses. Hematological malignancies are types of cancers that affect the blood, bone marrow, and/or lymph nodes. Examples of hematological malignancies that may be treated using romidepsin include, but are not limited to: acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), multiple myeloma, and myelodysplastic syndromes. In certain embodiments, the inventive combination is used to treat multiple myeloma. In certain particular embodiments, the cancer is relapsed and/or refractory multiple myeloma. In other embodiments, the inventive combination is used to treat chromic lymphocytic leukemia (CLL). In certain particular embodiments, the cancer is relapsed and/or refractory CLL. In other embodiments, the inventive combination is used to treat chromic myelogenous leukemia (CML). In certain embodiments, the inventive combination is used to treat acute lymphoblastic leukemia (ALL). In certain embodiments, the inventive combination is used to treat acute myelogenous leukemia (AML). In certain embodiments, the cancer is cutaneous T-cell lymphoma (CTCL). In other embodiments, the cancer is peripheral T-cell lymphoma (PTCL). In certain embodiments, the cancer is a myelodysplastic syndrome.

Other cancers besides hematological malignancies may also be treated using DAC inhibitors. In certain embodiments, the cancer is a solid tumor.

Exemplary cancers that may be treated using DAC inhibitor therapy, including combination therapy, include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, etc.

In certain embodiments, a DAC inhibitor is used to treat pancreatic cancer. In certain embodiments, a DAC inhibitor is used to treat prostate cancer. In certain specific embodiments, the prostate cancer is hormone refractory prostate cancer.

In certain embodiments, a DAC inhibitor is administered in combination with one or more additional therapeutic agents, e.g., another cytotoxic agent. Exemplary cytotoxic agents that may be administered in combination with a DAC inhibitor include gemcitabine, decitabine, and flavopiridol. In other embodiments, a DAC inhibitor is administered in combination with an anti-inflammatory agent such as aspirin, ibuprofen, acetaminophen, etc., pain reliever, anti-nausea medication, or anti-pyretic. In certain other embodiments, a DAC inhibitor is administered in combination with a steroidal agent (e.g., dexamethasone). In certain embodiments, a DAC inhibitor is administered in combination with an agent to treat gastrointestinal disturbances such as nausea, vomiting, and diarrhea. These additional agents may include anti-emetics, anti-diarrheals, fluid replacement, electrolyte replacement, etc. In other embodiments, a DAC inhibitor is administered in combination with electrolyte replacement or supplementation such as potassium, magnesium, and calcium, in particular, potassium and magnesium. In certain embodiments, a DAC inhibitor is administered in combination an antiarrhythmic agent. In certain embodiments, a DAC inhibitor is administered in combination with a platelet booster, for example, an agent that increases the production of platelets. In certain embodiments, a DAC inhibitor is administered in combination with an agent to boost the production of blood cells such as erythropoietin. In certain embodiments, a DAC inhibitor is administered in combination with an agent to prevent hyperglycemia. In certain embodiments, a DAC inhibitor is not administered with another HDAC or DAC inhibitor.

Pharmaceutical Compositions

In some embodiments, the present invention provides pharmaceutical compositions of electrolytes for administration with DAC (e.g., HDAC) inhibitors as provided herein. In some embodiments, inventive pharmaceutical compositions include electrolytes and one or more DAC (e.g., HDAC) inhibitors; in some embodiments, the electrolytes are formulated separately. In some embodiments, inventive pharmaceutical compositions are prepared in unit dosage forms. In general, a pharmaceutical composition of the present invention includes one or more active agents (i.e., one or more electrolytes and/or one or more DAC inhibitors) formulated with one or more pharmaceutically acceptable carriers or excipients.

In some embodiments, the pharmaceutically acceptable carrier is selected from the group consisting of sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions; non-toxic compatible lubricants such as sodium lauryl sulfate and magnesium stearate; coloring agents; releasing agents; coating agents; sweetening, flavoring and perfuming agents; preservatives and antioxidants; and combinations thereof. In some embodiments, the pH of the ultimate pharmaceutical formulation may be adjusted with pharmaceutically acceptable acids, bases or buffers to enhance the stability of the formulated compound or its delivery form.

Pharmaceutical compositions of this invention may be administered can be administered by any appropriate means including, for example, orally, parenterally, by inhalation spray, topically, rectally, nasally, buccally, vaginally or via an implanted reservoir. The term parenteral as used herein includes subcutaneous, intracutaneous, intravenous, intramuscular, intraarticular, intraarterial, intrasynovial, infrasternal, intrathecal, intralesional and intracranial injection or infusion techniques. In many embodiments, pharmaceutical compositions are administered orally or by injection in accordance with the present invention.

Liquid dosage forms for oral administration include pharmaceutically acceptable emulsions, microemulsions, solutions, suspensions, syrups and elixirs. In addition to the active agent(s), liquid dosage forms of pharmaceutical compositions may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. A sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from a site of subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form.

Alternatively, delayed absorption of a parenterally administered drug form can be accomplished by dissolving or suspending the drug in an oil vehicle. Injectable depot forms can be made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions that are compatible with body tissues.

Compositions for rectal or vaginal administration are typically suppositories which can be prepared by mixing the active agents with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include, for example, capsules, tablets, pills, powders, and granules. In such solid dosage forms, the active agent(s) is/are typically mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents, permeation enhancers, and/or other agents to enhance absorption of the active agent(s).

Solid compositions of a similar type may also be employed as fillers in soft and hard-filled gelatin capsules using such excipients as lactose or milk sugar as well as high molecular weight polyethylene glycols and the like.

Solid dosage forms such as tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In certain embodiments, oral dosage forms are prepared with coatings or by other means to control release of active agent (e.g., DAC or HDAC inhibitor) over time and/or location within the gastrointestinal tract. A variety of strategies to achieve such controlled (or extended) release are well known in the art, and are within the scope of the present invention.

Dosage forms for topical or transdermal administration include ointments, pastes, creams, lotions, gels, powders, solutions, sprays, inhalants or patches. In general, such preparations are prepared by admixing active agent(s) under sterile conditions with a pharmaceutically acceptable carrier and any needed preservatives or buffers as may be required.

Ophthalmic formulation, ear drops, eye ointments, powders and solutions are also contemplated as being within the scope of this invention.

Ointments, pastes, creams and gels may contain, in addition to active agent(s), excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to active agent(s), excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have often can provide controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, active agent(s) is/are formulated and administered to the patient in solid or liquid particulate form by direct administration e.g., inhalation into the respiratory system. Solid or liquid particulate forms of the active agent(s) prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

The total daily dose of any particular active agent administered to a human or other animal in single or in divided doses in accordance with the present invention can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses. In certain embodiments, about 10-100 mg of the compound is administered per day in single or multiple doses. In certain embodiments, about 100-500 mg of the compound is administered per day in single or multiple doses. In certain embodiments, about 250-500 mg of the compound is administered per day in single or multiple doses. In certain embodiments, about 500-750 mg of the compound is administered per day in single or multiple doses.

In the treatment of neoplasms such as cancer in a subject, a DAC inhibitor is typically dosed at 1-30 mg/m². In certain embodiments, a DAC inhibitor is dosed at 1-15 mg/m². In certain embodiments, a DAC inhibitor is dosed at 5-15 mg/m². In certain particular embodiments, a DAC inhibitor is dosed at 4, 6, 8, 10, 12, 14, 16, 18, or 20 mg/m². A DAC inhibitor is typically administered in a 28 day cycle with the agent being administered on days 1, 8 and 15. In certain embodiments, the DAC is administered on days 1 and 15 with day 8 being skipped. As would be appreciated by one of skill in the art, the dosage and timing of administration of the dosage of the DAC inhibitor may vary depending on the patient and condition being treated. For example, adverse side effects may call for lowering the dosage of DAC inhibitor administered.

Pharmaceutical compositions for use in accordance with the present invention can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, for example with a dosage ranging from about 0.1 to about 500 mg/kg of body weight, alternatively dosages between 1 mg and 1000 mg/dose, every 4 to 120 hours, or according to the requirements of the particular drug.

The methods herein contemplate administration of an effective amount of active agent or pharmaceutical composition sufficient for a desired or stated effect. Typically, the pharmaceutical compositions of this invention will be administered from about 1 to about 6 times per day or alternatively, as a continuous infusion. Such administration can be used as a chronic or acute therapy. The amount of any particular active agent that may be combined with pharmaceutically acceptable excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound. For romidepsin, preparations may contain about 20-50%, 25-45%, 30-40%, or approximately 32%, 33%, 34%, or 35% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When pharmaceutical compositions contain two or more active agents, it is generally the case that each agent is present at dosage levels of between about 1 to 100%, for example about 5 to 95%, of the level normally administered in a monotherapy regimen.

Particular formulations and dosing regimens have been established for a variety of HDAC inhibitors. For example, SAHA is commonly administered within a range of about 300-400 mg daily orally; PXD101 is commonly administered within a range of about up to 2000 mg/m²/day intravenously (e.g., on days 1 to 5 of a 21 day cycle), and may possibly be administered orally; MGCD0103 is commonly administered at doses up to about 27 mg/m² given orally (e.g., daily for about 14 days); LBH589 is commonly administered at doses up to about 14 mg/m² as an intravenous infusion (e.g., on days 1-7 of a 21 day cycle); MS-275 is commonly administered within a dose range of about 2-12 mg/m² intravenously (e.g., every 14 days).

In the treatment of neoplasms such as cancer in a subject, romidepsin is typically dosed at 0.5 mg/m² to 28 mg/m². In certain embodiments, the romidepsin is dosed in the range of 1 mg/m² to 25 mg/m². In certain embodiments, the romidepsin is dosed in the range of 0.5 mg/m² to 15 mg/m². In certain embodiments, the romidepsin is dosed in the range of 1 mg/m² to 15 mg/m². In certain embodiments, the romidepsin is dosed in the range of 1 mg/m² to 8 mg/m². In certain embodiments, the romidepsin is dosed in the range of 0.5 mg/m² to 5 mg/m². In certain embodiments, the romidepsin is dosed in the range of 2 mg/m² to 10 mg/m². In other embodiments, the dosage ranges from 10 mg/m² to 20 mg/m². In certain embodiments, the dosage ranges from 5 mg/m² to 10 mg/m². In other embodiments, the dosage ranges from 10 mg/m² to 15 mg/m². In still other embodiments, the dosage is approximately 8 mg/m². In still other embodiments, the dosage is approximately 9 mg/m². In still other embodiments, the dosage is approximately 10 mg/m². In still other embodiments, the dosage is approximately 11 mg/m². In still other embodiments, the dosage is approximately 12 mg/m². In still other embodiments, the dosage is approximately 13 mg/m². In still other embodiments, the dosage is approximately 14 mg/m². In still other embodiments, the dosage is approximately 15 mg/m². In certain embodiments, increasing doses of romidepsin are administered over the course of a cycle. For example, in certain embodiments, a dose of approximately 8 mg/m², followed by a dose of approximately 10 mg/m², followed by a dose of approximately 12 mg/m² may be administered over a cycle. As will be appreciated by one of skill in the art, depending on the form of romidepsin being administered the dosing may vary. The dosages given herein are dose equivalents with respect to the active ingredient, romidepsin. In certain embodiments, romidepsin is administered intravenously. In certain embodiments, the romidepsin is administered intravenously over a 0.5-6 hour time frame. In certain particular embodiments, the romidepsin is administered intravenously over 30 minutes to 2 hours. In certain particular embodiments, the romidepsin is administered intravenously over 30 minutes to 60 minutes. In certain particular embodiments, the romidepsin is administered intravenously over 60 minutes to 90 minutes. In certain particular embodiments, the romidepsin is administered intravenously over 90 minutes to 120 minutes. In certain particular embodiments, the romidepsin is administered intravenously over 2-3 hours. In certain particular embodiments, the romidepsin is administered intravenously over 3-4 hours. In certain particular embodiments, the romidepsin is administered intravenously over 5-6 hours. In certain embodiments, the romidepsin is administered one day followed by several days in which the romidepsin is not administered. In certain embodiments, romidepsin is administered twice a week. In certain embodiments, romidepsin is administered once a week. In other embodiments, romidepsin is administered every other week. In certain embodiments, romidepsin is administered on days 1, 8, and 15 of a 28 day cycle. In certain particular embodiments, an 8 mg/m² dose of romidepsin is administered on day 1, a 10 mg/m² dose of romidepsin is administered on day 8, and a 12 mg/m² dose of romidepsin is administered on day 15. In certain embodiments, romidepsin is administered on days 1 and 15 of a 28 day cycle with day 8 being skipped. The 28 day cycle may be repeated. In certain embodiments, the 28 day cycle is repeated 3-10 times. In certain embodiments, the treatment includes 5 cycles. In certain embodiments, the treatment includes 6 cycles. In certain embodiments, the treatment includes 7 cycles. In certain embodiments, the treatment includes 8 cycles. In certain embodiments, greater than 10 cycles are administered. As would be appreciated by one of skill in the art, the dosage and timing of administration of the dosage of romidepsin may vary depending on the patient and condition being treated. In certain embodiments, the cycles are continued as long as the patient is responding. The therapy may be terminated once there is disease progression, a cure or remission is achieved, or side effects become intolerable. Adverse side effects may also call for lowering the dosage of romidepsin administered.

Alternatively, romidepsin may be administered orally. In certain embodiments, romidepsin is dosed orally in the range of 10 mg/m² to 300 mg/m². In certain embodiments, romidepsin is dosed orally in the range of 25 mg/m² to 100 mg/m². In certain embodiments, romidepsin is dosed orally in the range of 100 mg/m² to 200 mg/m². In certain embodiments, romidepsin is dosed orally in the range of 200 mg/m² to 300 mg/m². In certain embodiments, romidepsin is dosed orally at greater than 300 mg/m². In certain embodiments, romidepsin is dosed orally in the range of 50 mg/m² to 150 mg/m². In other embodiments, the oral dosage ranges from 25 mg/m² to 75 mg/m², As will be appreciated by one of skill in the art, depending on the form of romidepsin being administered the dosing may vary. The dosages given herein are dose equivalents with respect to the active ingredient, romidepsin. In certain embodiments, romidepsin is administered orally on a daily basis. In other embodiments, romidepsin is administered orally every other day. In still other embodiments, romidepsin is administered orally every third, fourth, fifth, or sixth day. In certain embodiments, romidepsin is administered orally every week. In certain embodiments, romidepsin is administered orally every other week. The administration of romidepsin may be terminated once there is disease progression, a cure or remission is achieved, or side effects become intolerable.

Unless otherwise defined, all technical and scientific terms used herein are accorded the meaning commonly known to one of ordinary skill in the art. All publications, patents, published patent applications, and other references mentioned herein are hereby incorporated by reference in their entirety. The embodiments of the invention should not be deemed to be mutually exclusive and can be combined.

EXEMPLIFICATION

The present invention will be better understood in connection with the following Example, which is intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

EXAMPLE 1

Cardiac Side Effects Observed Upon Treatment with Romidepsin not Seen when Patients Receive Electrolyte Supplementation The present Example demonstrates that cardiac side effects that are observed with some patients receiving romidepsin therapy are not observed when patients receive electrolyte supplementation.

Methods Patients: Patients with relapsed or refractory cutaneous or relapsed peripheral T-cell lymphoma were enrolled in a phase II trial evaluating the safety and efficacy of romidepsin. The protocol (NCI 01-C-0049 or 1312) and informed consent were approved by the Institutional Review Board of the National Cancer Institute. All data used in this analysis were obtained from patients who signed an informed consent and were enrolled and treated at the NIH Warren Grant Magnuson Clinical Center. Toxicities were reported using the National Cancer Institute Common Toxicity Criteria, CTC version 2.0. The Inclusion Criteria required measurable disease, an age of 18 years or older, an ECOG performance status of 0, 1 or 2, and a life expectancy of >12 wk. Required laboratory values included AGC≥1000/μL, platelets≥100,000/μL, bilirubin <1.5× the institutional upper limit of normal (ULN), AST <3×ULN, and creatinine <1.5×ULN. Patients with a myocardial infarction within the previous 6 months, a left ventricular ejection fraction (LVEF) below normal (<45% if performed by MUGA, or <50% if performed by echocardiogram or cardiac MRI), a corrected QT interval of >500 ms, unstable angina, or third degree heart block (unless with pacemaker) were not eligible to enroll.

Dosing regimen: The first 5 patients enrolled in the protocol had treatment administered on days 1 and 5 of a 21-day cycle with a starting dose of 18 mg/m², using the original schedule piloted at the NCI. Subsequently, the protocol was amended and all patients were treated on days 1, 8 and 15 of a 28 day cycle, with a starting dose of 14 mg/m². This change was made for improved patient tolerability. In all cases, romidepsin was administered as a 4 hour intravenous (i.v.) infusion. Provisions for dose reduction were made in the case of grade 3 or 4 toxicity. Alternatively, a dose increase was allowed for patients who had no serious toxicities. Because some patients with observed cardiac effects had low potassium and magnesium levels, the protocol was later amended to mandate supplementation of electrolytes to achieve serum magnesium and potassium levels over 0.85 mmol/L and 4.0 mmol/L, respectively, prior to administration of romidepsin (aka depsipeptide).

Cardiac monitoring on protocol:
(1) ECGs: ECGs were obtained prior to starting therapy, prior to administration of each dose, within one hour after completion of the infusion and on the day following treatment. An additional ECG was obtained on day 3 of the first cycle. ECGs were obtained using an HP Pagewriter XLi or a GE Marquette MAC1200 and recorded at 25 mm/sec, with an amplitude of 10 mm/mV and with 60 Hz filtering. They were analyzed using Pagewriter A.04.01 ECG analysis software (Philips Medical Systems). The QT interval measurement in this program is made by averaging the five longest QT intervals with a T or T' wave amplitude greater than 0.15 mV. All ECGs were interpreted by a single cardiologist (D.R.R.) in a blinded fashion. T-wave and ST segment abnormalities were assessed by either R.L.P. or S.E.B. and grades were based on definitions in the National Cancer Institute Common Toxicity Criteria, version 2. Grade 1 toxicity was defined as nonspecific T-wave abnormalities, (flattening or inversion without ST segment abnormalities) and Grade 2 as ST segment depression of at least 1 mm in at least 2 leads. If both were observed, then the ECG was assigned a grade 2 toxicity. A more precise evaluation of the ECGs scored as grade 2 was carried out by D.R.R.

(2) QTc analysis: The heart rate-corrected QT interval (QTc), indicating repolarization time, was calculated using Bazett's formula (QT divided by the square root of the preceding R—R interval) using the ECG machine software. All ECGs with QTc of 480 ms or greater were reviewed by a cardiologist (D.R.R.). The QTc analysis was performed on ECGs obtained during the first six cycles from patients treated on the day 1, 8 and 15 schedule (37 patients). ECGs from patients with an intraventricular conduction delay, defined as QRS duration greater than 100 ms, were excluded from the QTc analysis since in that setting the QTc interval includes a variable depolarization interval that leads to a prolonged QTc value (22). Six patients met this criterion and were omitted, leaving ECGs from 31 patients included in the primary QTc analysis.

(3) Cardiac troponin I assay: Serum CPK and Troponin I levels were obtained prior to each dose and on the day after each dose. Assays were performed in the Warren Grant Magnuson Clinical Center clinical laboratories using the Abbott Laboratories MEIA assay. Since specimens that have not clotted completely can give false positive results, and samples were frequently drawn from lines flushed with heparin, abnormal tests were repeated for confirmation.

Post treatment evaluation of cardiac function (LVEF): Echocardiograms to evaluate cardiac function were also performed on the day following the last dose of the cycle; day 6 for patients treated on days 1 and 5, or day 16 for patients treated on days 1, 8 and 15.

Evaluation of left ventricular ejection fraction: LVEF evaluations were performed at baseline, after the second cycle and every 3 cycles thereafter using MUGA, echocardiogram or cardiac MRI (23, 24). A patient's on-study and last available LVEF are included in this analysis. Cardiac measurements were performed according to the American Society of Echocardiography guidelines (25). LVEFs from echocardiograms were evaluated by an independent reviewer in a blinded manner and were assessed using the biplane Simpson's method.

Rhythm: A 24-hour Holter monitor was obtained prior to initiating therapy to establish a baseline rhythm. Patients were monitored by telemetry following administration of the first dose until discharge on day 3.

Statistical methods: A global statistical analysis which compared baseline QTc with the QTc from ECGs obtained on the day following treatment, within a cycle for each of the cycles, was done using repeated measures analysis of variance (ANOVA). Individual differences between paired values were evaluated for the statistical significance of the change using a Wilcoxon signed rank test. The overall statistical significance for the comparison of changes in worst ECG grade between two time points was determined using an exact marginal homogeneity test (26). All p-values are two-tailed.

Results:

Patient characteristics: Data from 42 of the first 43 patients who enrolled on this protocol and received at least one cycle of therapy at the Clinical Center of the NIH are included in these analyses; one patient found to have an intracardiac tumor after enrollment was excluded. Among 42 patients, 25 men and 17 women, the median age was 56 (range 27-79). A summary of patient characteristics is presented in Table 1. These patients received a total of 282 cycles and a total of 736 doses. Sixteen patients with stable disease or partial or complete response received 6 or more cycles, including 8 patients on protocol for more than one year. Eight patients received less than 2 complete cycles. Twenty-two patients had received prior therapy that included doxorubicin at a median dose of 300 mg/m$^2$ (40540). All patients had mature T-cell lymphomas; 24 patients had cutaneous T-cell lymphoma and 18 patients had peripheral T-cell lymphomas. Observed toxicities were similar to those observed in the phase I trial and were primarily nausea and fatigue.

TABLE 1

Characteristics of 42 Patients

| Characteristic | Number of patients |
|---|---|
| Gender | |
| Male | 25 |
| Female | 17 |
| Diagnosis | |
| CTCL | 24 |
| PTCL | 18 |
| No Prior doxorubicin | 20 |
| Prior doxorubicin | 22 |
| ECOG | |
| 0 | 10 |
| 1 | 26 |
| 2 | 6 |

| Characteristic | Median (range) |
|---|---|
| Age | 56 (27-79) |
| Cycles | 4 (1-47) |
| Doses | 11 (2-93) |
| Time on protocol (months) | 3.6 (0.5-41) |

ECG evaluations, T wave and ST depression: In all, 2051 ECGs from 42 patients were reviewed. In relation to 736 doses of romidepsin (aka depsipeptide) administered, 1877 ECGs, 83% of the 2250 planned were obtained pre-treatment, post-treatment, and the day following treatment. ECGs were also obtained on the third day of the first cycle. Among these, 649 were obtained prior to drug infusion, 630 ECGs were obtained within one hour following completion of the infusion, and 598 ECGs were obtained on the day following treatment. An additional 31 ECGs were obtained on the third day of the first cycle. The remaining 143 ECGs were obtained at unscheduled times.

T-wave (grade 1) or ST segment (grade 2) abnormalities noted on ECGs related to all administered doses are summarized in Table 2A and related to administration of the first does in Table 2B. Reviewing ECGs from all doses administered, 22% had grade 1 and 2% had grade 2 abnormalities prior to infusion of romidepsin (aka depsipeptide), and 48% had grade 1 and 3% had grade 2 abnormalities on ECGs obtained immediately after completion of infusion.

More marked ECG abnormalities were observed on the day following treatment, with 69% having grade 1 and 11% having grade 2 abnormalities. With the administration of the first dose, grade 1 ECGs abnormalities, consisting of T-wave flattening, were noted in 5% (2) of patients prior to initiating protocol, in 18% immediately post-infusion, in 44% on the day after treatment and in 45% on day 3 after treatment. Of note, ST segment depression, grade 2, was only detected in a few of the ECGs obtained on day 2 and was not observed on day 3. Similar results were observed when only the ECGs from the 37 patients treated on the day 1, 8, and 15 schedule were evaluated.

Ascertaining the worst ECG grade observed at any time during treatment for each of the 42 patients, 45% had grade 1 and 52% had grade 2 abnormalities at some point (Table 2C). Similar results, 43% and 54%, respectively, were obtained when evaluating ECGs obtained from the 37 patients treated on the day 1, 8, and 15 schedule.

Thus, the majority of ECGs demonstrated some T-wave or ST segment abnormality after administration of romidepsin.

TABLE 2A

Summary of T-wave and ST segment abnormalities associated with depsipeptide (n = 42)

| | # of ECGs | Grade 0 | Grade 1 | Grade 2 |
|---|---|---|---|---|
| Pre-treatment | 649 | 76% | 22% | 2% |
| Immediate post | 630 | 49% | 48% | 3% |
| Day after | 598 | 20% | 69% | 11% |

TABLE 2B

ECG abnormalities associated with the first dose of the first cycle (n = 42)

| | # of ECGs | Grade 0 | Grade 1 | Grade 2 |
|---|---|---|---|---|
| Pre | 42 | 95% | 5% | |
| Post | 39 | 82% | 18% | |
| Day 2 | 41 | 49% | 44% | 7% |
| Day 3 | 31 | 55% | 45% | |

TABLE 2C

ECG abnormalities associated with the indicated cycle of therapy.

| | # of Patients | Grade 0 | Grade 1 | Grade 2 |
|---|---|---|---|---|
| Cycle 1 only | 42 | 19% | 57% | 24% |
| All cycles | 42 | 2% | 45% | 52% |

To determine whether the observed ECG changes had resolved at the time patients presented for their next dose or new cycle, the ECG grade from the 37 patients treated on the day 1, 8, and 15 schedule were evaluated.

Upon presentation for treatment on day 8, the ECGs of nine of 18 patients who had grade 1 and two of three patients who had grade 2 abnormalities after their first dose had reverted to normal (Table 3A). Among 16 patients who had no abnormalities surrounding the day 1 dose, two returned with grade 1 abnormalities (overall test for changes in grade: p=0.0248). Similar results were observed when patients returned for day 15 treatment (Table 3A; overall test for changes in grade: p=0.0033).

The ECG grade at the time patients returned for the next cycle of therapy was also evaluated. Twenty-eight of the 34 patients returning for the second cycle of therapy had no evidence of T-wave or ST-segment abnormalities; these included 18 of 21 patients who had grade 1, and 4 of 7 patients who had grade 2 ECG abnormalities in the first cycle. Six patients with persistent abnormalities had the same or improved ECG grade. One patient with a grade 1 ECG at baseline was scored as grade 2 in the first cycle and returned for cycle 2 with a grade 2 ECG. Data from later cycles are presented in Table 3B (all p<0.0001 for comparisons noted for changes in grade for all three cycles compared) and suggest similar trends. ECGs scored as grade 2 were reviewed by a cardiologist for changes consistent with evidence of ischemia defined as 1 mm of ST segment depression 80 msec after the end of the QRS segment. Thirty-one of 69, 45%, met these criteria.

These observed ECG abnormalities raised the question of whether myocardial damage or dysfunction would be associated with the administration of romidepsin.

TABLE 3A

Shift tables showing the relationship between the worst ECG abnormalities following a dose of depsipeptide and the ECG grade observed at presentation for the next dose.

| | Pre-treatment day 8 (n = 37) | | |
|---|---|---|---|
| Grade | 0 | 1 | 2 |
| Worst grade post-day 1 treatment | | | |
| 0 | 14 | 2 | |
| 1 | 9 | 8 | 1 |
| 2 | 2 | 1 | |

| | Pre-treatment day 15 (n = 36) | | |
|---|---|---|---|
| Grade | 0 | 1 | 2 |
| Worst grade post-day 8 treatment | | | |
| 0 | 6 | 3 | |
| 1 | 13 | 10 | |
| 2 | 2 | 1 | 1 |

TABLE 3B

Shift tables showing the relationship between the worst ECG abnormali a cycle and the ECG grade observed at presentation for the next cycle of therapy.

| | Pre-treatment cycle 2 day 1 (n = 34) | | |
|---|---|---|---|
| Grade | 0 | 1 | 2 |
| Worst grade cycle 1 | | | |
| 0 | 6 | | |
| 1 | 18 | 3 | |
| 2 | 4 | 2 | 1 |

| | Pre-treatment cycle 3 day 1 (n = 28) | | |
|---|---|---|---|
| Grade | 0 | 1 | 2 |
| Worst grade cycle 2 | | | |
| 0 | 2 | | |
| 1 | 16 | 1 | |
| 2 | 7 | 2 | |

| | Pre-treatment cycle 4 day 1 (n = 20) | | |
|---|---|---|---|
| Grade | 0 | 1 | 2 |
| Worst grade cycle 3 | | | |
| 0 | | | |
| 1 | 14 | | |
| 2 | 6 | | |

Evaluations for Evidence of Myocardial Damage or Alteration of Cardiac Function:

Troponin evaluations: To evaluate myocardial damage as an etiology of the ECG abnormalities, serum cardiac troponin I (cTnI) levels were obtained prior to the administration of romidepsin (aka depsipeptide) (601 samples) and on the day following treatment (590 samples). As itemized in Table 4, 10 cTnI samples from 8 patients were found to be elevated; 3 (3.4-11.3 ng/ml) were obtained pre-treatment and were negative ($\leq 0.2$) upon repeat. Three elevated levels (2.1-3.3)

obtained the day after therapy were repeated the same day and found to be negative (≤0.2). Four were not rechecked, but troponin elevations did not occur with subsequent doses. CPK samples obtained in parallel with these 10 elevated cTnI samples were unchanged from pre-treatment, (range 16-200). Of note, troponin levels coincident with all ECGs scored as grade 2, and in 18 cases on the day following those ECGs, were within normal limits. It was concluded that the troponin elevations in these patients were false positive values.

TABLE 4

Troponin elevation detected among 1191 samples obtained.

| Troponin | | | CPK | |
|---|---|---|---|---|
| Pre-treatment | Repeat | Post-treatment | Pre-treatment | Post-treatment |
| 3.4 | ≤0.2 | ≤0.2 | 39 | N.D. |
| 6.4 | ≤0.2 | N.D. | 160 | 162 |
| 11.3 | ≤0.2 | ≤0.2 | 29 | 20 |

| Troponin | | | CPK | |
|---|---|---|---|---|
| Pre-treatment | Post-treatment | Repeat | Pre-treatment | Post-treatment |
| ≤0.2 | 3.3 | ≤0.2 | 43 | 28 |
| ≤0.2 | 2.1 | ≤0.2 | 27 | 18 |
| ≤0.2 | 2.6 | ≤0.2 | 47 | 16 |
| ≤0.2 | 8.3 | N.D. | 70 | 85 |
| ≤0.2 | 2.3 | N.D. | 200 | 157 |
| ≤0.2 | 15.8 | N.D. | 179 | 144 |
| ≤0.2 | 3.6 | N.D. | 28 | 28 |

N.D. Not Done

Post-treatment global LV function: To determine whether the observed ECG abnormalities were associated with acute LV wall motion abnormalities, echocardiograms were performed on the day following the last dose of the cycle (d 6 for patients treated on days 1 and 5, and day 16 for patients treated on days 1, 8, and 15). None of the 145 echocardiograms obtained from 34 patients demonstrated a change from baseline. Among 123 ECGs obtained on the same day as the day 6 or day 16 echocardiograms, 23 had ST-segment depression, 82 demonstrated T-wave flattening, and 18 had no abnormalities. These results further support the conclusion that the observed ECG abnormalities do not reflect a change in cardiac function.

Cardiac function evaluations: To assess left ventricular dysfunction, 159 LVEF evaluations were performed by MUGA, echocardiogram or cardiac MRI. All 42 patients underwent pre-protocol LVEF evaluations. Due to the different reference values and methodologies, we evaluated the data from patients who had MUGAs (19) separately from patients who had echocardiograms or cardiac MRIs (23), as summarized in Tables 5A and B. Seven patients did not complete a full 2 cycles and did not undergo a follow-up cardiac evaluation. All others had at least one follow-up exam. The data in Table 5 are from the last follow-up exam to allow assessment of function after the patient had received the most romidepsin (aka depsipeptide) possible.

For patients with MUGA scans, the median time to last scan from on-study for the 13 patients with both values was 20.3 weeks, with a range from 7 to 154 weeks. The median actual change in LVEF was 1%, with a range from minus (−)10% to 11%. The Wilcoxon signed rank p-value for the change was 0.87; thus, no statistically significant difference was detected between the on-study and the last measured ejection fraction.

For the patients followed by echocardiograms, the median time to last scan from on-study for the 22 patients with both values was 18.4 weeks, with a range from 4 weeks to 55 weeks. The echocardiograms were evaluated by an independent reviewer in a blinded manner. The median actual change in LVEF was −1%, with a range from −17% to 19%. The Wilcoxon signed rank p-value for the change was 0.25; thus, there is no statistically significant difference between the on-study and the last measured ejection fraction.

TABLE 5A

EF evaluations by MUGA in 20 patients

| | No. of Pts | On-study Median (range) | Last evaluation Median (range) | Time (mo.) Median (range) |
|---|---|---|---|---|
| All patients | 19 | 61% (46-85) | | |
| Patients with pre- and post treatment evaluations | 13 | 62% (46-85) | 61% (50-91) | 4.7 (2-35) |
| Patients treated with >6 cycles | 7 | 64% (50-77) | 61% (50-68) | 14 (5-35) |

TABLE 5B

EF evaluations by Echocardiogram in 22 patients

| | No. of Pts | On-study Median (range) | Last evaluation Median (range) | Time (mo.) Median (range) |
|---|---|---|---|---|
| All patients | 23 | 67% (53-85) | | |
| Patients with pre- and post treatment evaluations | 22 | 67% (53-85) | 64% (53-87) | 4.2 (1-13) |
| Patients treated with >6 cycles | 9 | 69% (56-85) | 68% (58-80) | 8.5 (5-13) |

Evaluation of patients treated for more than six cycles: Sixteen patients received six or more cycles of therapy (6-47), with a median cumulative dose of 390 mg/m$^2$ (164-1674), or 705 mg (269-3761), of romidepsin. Their LVEF evaluations did not demonstrate a change from baseline. Of these patients, 8 (50%) had prior therapy that included doxorubicin at an estimated cumulative prior doxorubicin dose of 300 mg/m$^2$ (80-400). These eight patients also did not demonstrate a difference in pre-treatment and post-treatment LVEF (Table 5C).

TABLE 5C

LVEF evaluations on patients receiving at least 6 cycles of therapy.

| Age | Prior dox (mg/m$^2$) | Cycles | Doses | Total DP (mg/m$^2$) | Starting EF | Latest EF | Time Diff (mo.) |
|---|---|---|---|---|---|---|---|
| 41* | 300 | 47 | 93 | 1674 | 50% | 61% | 30 |
| 57 | 120 | 8 | 16 | 164 | 77% | 68% | 6 |
| 64* | 80 | 32 | 64 | 909 | 54% | 64% | 35 |

TABLE 5C-continued

LVEF evaluations on patients receiving at least 6 cycles of therapy.

|  | Age | Prior dox (mg/m$^2$) | Cycles | Doses | Total DP (mg/m$^2$) | Starting EF | Latest EF | Time Diff (mo.) |
|---|---|---|---|---|---|---|---|---|
|  | 56 |  | 7 | 21 | 294 | 64% | 60% | 5 |
|  | 42* |  | 13 | 36 | 333 | 52% | 50% | 16 |
|  | 61 |  | 7 | 21 | 291 | 69% | 78% | 6 |
|  | 27 | 300 | 13 | 39 | 459 | 56% | 61% | 9 |
|  | 53 |  | 16 | 47 | 529 | 67% | 61% | 14 |
|  | 34 |  | 13 | 39 | 557 | 70% | 72% | 13 |
|  | 54 |  | 12 | 36 | 500 | 85% | 68% | 11 |
|  | 55 |  | 6 | 18 | 305 | 68% | 68% | 6 |
|  | 59* | 150 | 12 | 35 | 448 | 85% | 80% | 11 |
|  | 55 | 300 | 11 | 33 | 459 | 58% | 58% | 12 |
|  | 69 |  | 7 | 21 | 326 | 59% | 58% | 8 |
|  | 79* | 300 | 6 | 18 | 203 | 70% | 70% | 9 |
|  | 63 | 400 | 6 | 18 | 294 | 64% | 63% | 5 |
| Median | 55.5 | 300 | 11.5 | 34 | 390 | 65.5% | 63.5% | 9.8 |
| Range | 27-79 | 80-400 | 6-47 | 16-93 | 164-1674 | 50-85% | 50-80% | 5-35 |

Order of enrollment
*Patients remaining on study

QTc evaluation: There is no consensus as to what absolute QTc value or change of QTc from baseline should be used to evaluate drugs in development. Recommended parameters for evaluation include QTc values greater than 500, 480, or 450 ms or QTc interval increases from baseline of greater than 60 or 30 ms (27, 28).

QTc values greater than 450 ms were detected in 163 (8.0%) ECGs from 28 patients, greater than 480 ms in 20 (1%) ECGs from 10 patients, and greater than 500 ms in 5 (0.2%) ECGs from 4 patients. Eighty-nine percent of ECGs with QTc values over 450 ms were obtained either immediately post treatment or on the day following treatment. Of note, 2 of the four patients with QTc greater than 500 ms had an intraventricular conduction delay detected on ECGs obtained prior to initiation of protocol.

It has been shown that Bazett's formula overestimates the QTc at higher heart rates (29). All ECGs with QTc greater than 450 ms were associated with a HR of 60 beats per minute or greater and 99% with a HR of 80 beats per minute or greater. When all QTc were re-calculated using Friderica's formula, QTc values greater than 450 ms were detected in 27 (1.3%) ECGs from 15 patients, greater than 480 ms in 3 (0.1%) ECGs obtained from 3 patients, no QTc was greater than 500 ms.

To determine the statistical significance of changes of QTc from baseline, a formal analysis was carried out on Bazett calculated QTc values from ECGs obtained during the first six cycles of therapy in patients treated on the day 1, 8 and 15 schedule. ECGs obtained pre-treatment, post-treatment, and the day following treatment were included in this analysis, as well as ECGs obtained on the third day of the first cycle. ECGs from patients demonstrating a baseline intraventricular conduction delay were excluded. Thus, the ECG set comprised 349 doses administered to 31 patients.

Among 1078 expected ECGs, 1051 (97.5%) were obtained and available for evaluation. Initial analysis revealed that there was no statistically significant difference among the QTc values obtained at the beginning of each cycle (p=0.98). Further analysis demonstrated that there was no statistical difference in QTc obtained prior to the administration of each dose within a cycle. This indicates that any change of QTc from baseline did not persist from one cycle to the next or from one dose to the next dose. The mean corrected QT interval values for all pre-treatment ECGs on days 1, 8 and 15, and post-treatment, ECGs obtained on days 2, 9, and 16, are shown in Table 6A. In this analysis, the mean value for the QTc on ECGs obtained on the day after treatment was longer, p<0.0001, than the mean value of the QTc on ECGs obtained prior to treatment.

Because the QTc values obtained at the beginning of each cycle were not statistically different, a mean pre-cycle QTc was determined for each patient and defined as baseline. Differences in the corrected QT interval are presented in Table 6B. A median increase of 16.5 ms (−12.5 to 29.5, p<0.0001) was observed on ECGs obtained immediately post-treatment after the first dose of the first cycle and 10.8 ms (−33.7 to 78.3, p<0.0009) on the ECGs obtained on day 2 of the first cycle. Similar changes in QTc were detected after treatment with the second and third dose of the cycle (data not shown) and on subsequent cycles (Table 6B). No statistically significant difference was observed between the QTc on the ECG obtained immediately post-treatment and the QTc on the ECG obtained day 2 post-treatment ([D2]−[4 hr], p=0.98).

QTc values from ECGs obtained on day 3 were statistically lower than those obtained on day 2 (p=0.0009), and similar to those obtained pre-treatment (p=0.25), indicating that any changes observed with treatment and within the first 24 hour period had reverted to baseline by 48 hours after treatment. Overall, 514 of 670 ECGs obtained immediately post-treatment or on the day following treatment demonstrated an increased QTc from baseline, median: 13.42 ms, range: −49.00 to +78.25.

The maximum increase in QTc was 78.25 ms, which represented an increase of 19% over that patient's mean baseline QTc of 415.75. The maximal increase of QTc ranged from 3 to 19%, with a median of 11.3%. In this set, 25% and 2.6% of the doses were associated with a 30 to 60 ms and a greater than 60 ms prolongation of QTc, respectively. Similar results were obtained when this evaluation was performed on ECGs obtained in the first 6 cycles from all 42 patients with 24% and 3.2% of the doses associated with a 30 to 60 ms and a greater than 60 ms prolongation of QTc, respectively.

TABLE 6A

Least Square mean QT interval values for all doses of the first 6 cycles of 31 patients as estimated by repeated measures ANOVA

|  | n | Mean | SEM |
|---|---|---|---|
| day 1 | 122 | 410.3 | 1.92 |
| day 2 | 117 | 422.7 | 1.95 |
| day 8 | 117 | 410.8 | 1.94 |
| day 9 | 110 | 426.0 | 1.98 |

TABLE 6A-continued

Least Square mean QT interval values for all doses of the first 6 cycles of 31 patients as estimated by repeated measures ANOVA

|  | n | Mean | SEM |
|---|---|---|---|
| day 15 | 110 | 408.0 | 1.99 |
| day 16 | 104 | 423.7 | 2.03 |
| Pre-dose | 349 | 409.7 | 1.55 |
| Post dose | 331 | 424.1* | 1.57 |

*p < 0.0001

TABLE 6B

Differences in corrected QT intervals

| QTc Interval Difference | n | Median (msec) | Range | p-value |
|---|---|---|---|---|
| [4 hr]-[Baseline] | | | | |
| C1 | 29 | 16.5 | −12.5 to 29.5 | <0.0001 |
| C2 | 28 | 8.0 | −21.5 to 34.7 | 0.0006 |
| C3 | 20 | 15.5 | −22.5 to 49.0 | 0.002 |
| C4 | 16 | 15.9 | −22.5 to 30.8 | 0.002 |
| C5 | 11 | 18.2 | −0.5 to 26.0 | 0.002 |
| C6 | 13 | 18.8 | −5.5 to 49.0 | 0.003 |
| [D2]-[Baseline] | | | | |
| C1 | 30 | 10.8 | −33.7 to 78.3 | 0.0009 |
| C2 | 28 | 13.2 | −18.5 to 35.5 | 0.004 |
| C3 | 20 | 5.3 | −23.5 to 46.3 | 0.28 |
| C4 | 16 | 15.5 | −15.5 to 53.3 | 0.006 |
| C5 | 11 | 14.8 | −10.5 to 70.5 | 0.032 |
| C6 | 12 | 17.8 | −22.5 to 48.0 | 0.096 |
| [D2]-[4 hr] | | | | |
| C1 | 29 | 0.0 | −45.0 to 75.0 | 0.98 |
| [D3]-[Baseline] | | | | |
| C1 | 23 | −2.5 | −32.2 to 29.0 | 0.25 |
| [D3]-[D2] | | | | |
| C1 | 22 | −20.0 | −63.0 to 50.0 | 0.0009 |

Rhythm evaluations: Pre-treatment Holter monitoring was obtained in 37 of the 42 patients. Supraventricular tachycardia (SVT) or ventricular tachycardia (VT) defined as more than three consecutive aberrant beats, was noted in a significant percentage of patients, with SVT noted in 14 (38%) patients and VT noted in 5 (14%) patients with 4 (11%) patients having both. Supraventricular or ventricular ectopy was also frequently noted prior to initiation of romidepsin (aka depsipeptide) therapy, with 24 (65%) and 14 (38%) patients found to have more than one SVE or VE beat per hour, respectively.

Twenty-four hour Holter monitoring was performed during 20 administrations of romidepsin (aka depsipeptide) to 9 patients, providing additional safety information. Two patients were noted to have SVT; however, these episodes were similar to those observed on the pretreatment Holter. No patient had VT, including 2 patients observed to have VT pre-treatment.

Telemetry monitoring for 24-36 hours was performed on 36 patients during and after administration of romidepsin (aka depsipeptide). One patient had significant ectopy prior to starting therapy, with VT, SVT and episodes of accelerated idioventricular rhythm. This patient underwent both pre treatment and post treatment electrophysiologic studies that demonstrated no inducibility. Three additional patients were observed to have rare SVT. These patients were noted to have SVT and supraventricular ectopy of similar frequency on pre-treatment Holter. Four additional patients were observed to have wide complex tachycardia with a maximum frequency of one event per 24 hr period and length of 4 to 12 beats, all similar to that observed on pre-treatment Holters.

Cardiac events observed on trial: The one patient excluded from the data analysis was a 62 year old patient who was found to have a true positive elevated troponin after receiving the first dose of his second cycle of romidepsin (aka, depsipeptide). Cardiac evaluation included a cardiac MRI that detected an intracardiac mass that was later confirmed to be T-cell lymphoma. This patient was then removed from study.

One of the patients found to have a QTc greater than 500 was then placed on telemetry and was observed to have 12 beat run of VT that was asymptomatic and did not recur. Concurrently, this patient had abnormal magnesium and potassium levels that may have been related to her lymphoma, prior chemotherapy, or underlying celiac disease.

Four additional patients with VT were identified as described above. The only patient with significant ectopy had ventricular trigeminy. This patient was noted to have significant ventricular ectopy on the pre-treatment Holter monitor. Furthermore, this patient also was noted to have below normal potassium and magnesium levels. At that time our cardiologist recommended maintaining this patient's potassium and magnesium levels in the high normal range. The decision was then made to incorporate this into the protocol for all of the patients.

Another patient developed atrial fibrillation. This patient had a history of COPD and premature atrial contractions on Holter monitor prior to treatment with romidepsin. One patient found to have significant ectopy prior to initiation of protocol was subjected to pre-treatment and post-treatment EP studies that demonstrated no change in intracardiac conduction or inducibility of any arrhythmias.

REFERENCES

1. Sandor, V, Senderowicz, A, Mertins, S, et al. P21-dependent G(1) arrest with downregulation of cyclin D1 and upregulation of cyclin E by the histone deacetylase inhibitor FR901228. Br J Cancer 2000; 83: 817-825.
2. Richon, V M, Sandhoff, T W, Rifkind, R A, and Marks, P A Histone deacetylase inhibitor selectively induces p21 WAF 1 expression and gene-associated histone acetylation. Proc Natl Acad Sci USA 2000; 97: 10014-10019.
3. Qiu, L, Burgess, A, Fairlie, D P, Leonard, H, Parsons, P G, and Gabrielli, B G Histone deacetylase inhibitors trigger a G2 checkpoint in normal cells that is defective in tumor cells. Mol Biol Cell 2000; 11: 2069-2083.
4. Gu, W and Roeder, R G Activation of p53 sequence-specific DNA binding by acetylation of the p53 C-terminal domain. Cell. 1997; 90: 595-606.
5. Wang, C, Fu, M, Angeletti, R H, et al. Direct acetylation of the estrogen receptor alpha hinge region by p300 regulates transactivation and hormone sensitivity. J Biol Chem 2001; 276: 18375-18383.
6. Piekarz, R L, Robey, R W, Zhan, Z R, et al. T-cell lymphoma as a model for the use of histone deacetylase inhibitors in cancer therapy: Impact of depsipeptide on molecular markers, therapeutic targets, and mechanisms of resistance. Blood 2004; 103: 4636-4643.
7. Peart, M J, Tainton, K M, Ruefli, A A, et al. Novel mechanisms of apoptosis induced by histone deacetylase inhibitors. Cancer Res 2003; 63: 4460-4471.

8. Marks, P A, Richon, V M, and Rifkind, R A Histone deacetylase inhibitors: Inducers of differentiation or apoptosis of transformed cells. J Natl Cancer Inst 2000; 92: 1210-1216.
9. Byrd, J C, Shinn, C, Ravi, R, et al. Depsipeptide (FR901228): A novel therapeutic agent with selective, in vitro activity against human B-cell chronic lymphocytic leukemia cells. Blood 1999; 94: 1401-1408.
10. Kim, Y B, Lee, K H, Sugita, K, Yoshida, M, and Horinouchi, S Oxamflatin is a novel antitumor compound that inhibits mammalian histone deacetylase. Oncogene 1999; 18: 2461-2470.
11. Marshall, J L, Rizvi, N, Kauh, J, et al. A phase I trial of depsipeptide (FR901228) in patients with advanced cancer. J Exp Ther Oncol. 2002; 2: 325-332.
12. Piekarz, R L, Robey, R, Sandor, V, et al. Inhibitor of histone deacetylation, depsipeptide (FR901228), in the treatment of peripheral and cutaneous T-cell lymphoma: A case report. Blood 2001; 98: 2865-2868.
13. Sandor, V, Bakke, S, Robey, R W, et al. Phase I trial of the histone deacetylase inhibitor, depsipeptide (FR901228, NSC 630176), in patients with refractory neoplasms. Clin Cancer Res 2002; 8: 718-728.
14. Keefe, D L The cardiotoxic potential of the 5-HT3 receptor antagonist antiemetics: Is there cause for concern? Oncologist 2002; 7: 65-72.
15. Ewer, M S and Lippman, S M Type II chemotherapy-related cardiac dysfunction: Time to recognize a new entity. J Clin Oncol 2005; 23: 2900-2902.
16. Ewer, M S, Gibbs, F I R, Swafford, J, and Benjamin, R S Cardiotoxicity in patients receiving transtuzumab (Herceptin): Primary toxicity, synergistic or sequential stress, or surveillance artifact? Semin Oncol 1999; 26: 96-101.
17. Seidman, A, Hudis, C, Pierri, M K, et al. Cardiac dysfunction in the trastuzumab clinical trials experience. J Clin Oncol 2002; 20: 1215-1221.
18. Speyer, J Cardiac dysfunction in the trastuzumab clinical experience. J Clin Oncol 2002; 20: 1156-1157.
19. Lenihan, D J, Alencar, A J, Yang, D, Kurzrock, R, Keating, M I, and Duvic, M Cardiac toxicity of alemtuzumab in patients with mycosis fungoides/Sezary syndrome. Blood 2004; 104: 655-658.
20. Barbey, J T, Pezzullo, J C, and Soignet, S L Effect of arsenic trioxide on QT interval in patients with advanced malignancies. J Clin Oncol 2003; 21: 36093615.
21. University of Arizona Center for Education and Research on Therapeutics. www.torsades.org.
22. Das, G QT interval and repolarization time in patients with intraventricular conduction delay. J Electrocardiol 1990; 23: 49-52.
23. Borer, J S, Bacharach, S L, Green, M V, Kent, K M, Epstein, S E, and Johnston, G S Real-time radionuclide cineangiography in noninvasive evaluation of global and regional left-ventricular function at rest and during exercise in patients with coronary-artery disease. N Engl J Med 1977; 296: 839-844.
24. Sierra-Galan, L M, Ingkanisorn, W P, Rhoads, K L, Agyeman, K O, and Arai, A E Qualitative assessment of regional left ventricular function can predict MRI or radionuclide ejection fraction: An objective alternative to eyeball estimates. J Cardiovasc Magn Reson 2003; 5: 451-463.
25. Schiller, N B, Shah, P M, Crawford, M, et al. Recommendations for quantitation of the left ventricle by two-dimensional echocardiography. American Society of Echocardiography Committee on Standards, Subcommittee on Quantitation of Two-Dimensional Echocardiograms. J Am Soc Echocardiogr 1989; 2: 358-367.
26. A Agresti. Categorical data analysis. New York: Wiley; 1990. p. 347-375.
27. The clinical evaluation of QT/QTc interval prolongation and proarrhythmic potential for non-antiarrhythmic drugs. 10 Jun. 2004. http://www.fda.gov/cber/gdlns/iche14qtc.htm.
28. Moss, A J Measurement of the QT interval and the risk associated with QTc interval prolongation: A review. Am J Cardiol 1993; 72: 23B-25B.
29. Sagie, A, Larson, M G, Goldberg, R J, Bengtson, J R, and Levy, D An improved method for adjusting the QT interval for heart rate (the Framingham Heart Study). Am J Cardiol 1992; 70: 797-801.
30. Shan, K, Lincoff, A M, and Young, J B Anthracycline-induced cardiotoxicity. Ann Intern Med 1996; 125: 47-58.
31. Singal, P K and Iliskovic, N Doxorubicin-induced cardiomyopathy. N Engl J Med 1998; 339: 900-905.
32. Swain, S M, Whaley, F S, and Ewer, M S Congestive heart failure in patients treated with doxorubicin: A retrospective analysis of three trials. Cancer 2003; 97: 2869-2879.
33. Gottdiener, J S, Appelbaum, F R, Ferrans, V J, Deisseroth, A, and Ziegler, J Cardiotoxicity associated with high-dose cyclophosphamide therapy. Arch Intern Med 1981; 141: 758-763.
34. Herman, E H, Lipshultz, S E, Rifai, N, et al. Use of cardiac troponin T levels as an indicator of doxorubicin-induced cardiotoxicity. Cancer Res 1998; 58: 195-197.
35. Herman, E H, Zhang, J, Lipshultz, S E, et al. Correlation between serum levels of cardiac troponin-T and the severity of the chronic cardiomyopathy induced by doxorubicin. J Clin Oncol 1999; 17: 2237-2243.
36. Cardinale, D, Sandri, M T, Martinoni, A, et al. Myocardial injury revealed by plasma troponin I in breast cancer treated with high-dose chemotherapy. Ann Oncol 2002; 13: 710-715.
37. Missov, E, Calzolari, C, Davy, J M, Leclercq, F, Rossi, M, and Pau, B Cardiac troponin I in patients with hematologic malignancies. Coron Artery Dis 1997; 8: 537-541.
38. Bednar, M M, Harrigan, E P, and Ruskin, J N Torsades de pointes associated with nonantiarrhythmic drugs and observations on gender and QTc. Am J Cardiol 2002; 89: 1316-1319.
39. Morganroth, J Relations of QT(c) prolongation on the electrocardiogram to torsades-de-pointes—definitions and mechanisms. Am J Cardiol 1993; 72: B10B13.
40. Roden, D M Drug-induced prolongation of the QT interval. N Engl J Med 2004; 350: 1013-1022.
41. Morgan, M, Maloney, D, and Duvic, M Hypomagnesemia and hypocalcemia in mycosis fungoides: A retrospective case series. Leuk Lymphoma 2002; 43: 12971302.
42. Piekarz, R and Bates, S A review of depsipeptide and other histone deacetylase inhibitors in clinical trials. Curr Pharm Des 2004; 10: 2289-2298.
43. Bednar, M M, Harrigan, E P, Anziano, R J, Camm, A J, and Ruskin, J N The QT interval. Prog Cardiovasc Dis 2001; 43: 1-45.
44. Shiraga, T, Tozuka, Z, Ishimura, R, Kawamura, A, and Kagayama, A Identification of cytochrome P450 enzymes involved in the metabolism of FK228, a potent histone deacetylase inhibitor, in human liver microsomes. Biol Pharm Bull 2005; 28: 124-129.
45. Duvic, M, Talpur, R, Chiao, N, and Chiao, J Phase II trial of oral suberoylanilide hydroxamic acid (SAHA) for cutaneous T-cell lymphoma and peripheral T-cell lymphoma. Blood 2003; 102: 179a.
46. Kelly, W K, Richon, V M, O'Connor, O, et al. Phase I clinical trial of histone deacetylase inhibitor: Suberoylanilide hydroxamic acid administered intravenously. Clin Cancer Res 2003; 9: 3578-3588.
47. Rowinsky, EKJdB, D. J. Deangelo, A. van Oosterom, et al. Cardiac monitoring in phase I trials of a novel histone deacetylase (HDAC) inhibitor LAQ824 in patients with advanced solid tumors and hematologic malignancies. J Clin Oncol 2005; 22: Abstract #3131.
48. Ryan, Q C, Headlee, D, Acharya, M, et al. Phase I and pharmacokinetic study of MS-275, a histone deacetylase inhibitor, in patients with advanced and refractory solid tumors or lymphoma. J Clin Oncol 2005; 23: 3912-3922.
49. Steele, N, L. Vidal, J. Plumb, et al. A phase 1 pharmacokinetic and pharmacodynamic study of the histone deacetylase inhibitor PXD101 in patients with advanced solid tumours. J Clin Oncol 2005; 22: 3035.
50. Fischer, T, A. Patnaik, K. Bhalla, et al. Results of cardiac monitoring during phase I trials of a novel histone deacetylase inhibitor LBH589 in patients with advanced solid tumors and hematologic malignancies. J Clin Oncol 2005; 3106.
51. Sundaram, S and Goldberger, J J Risk stratification and epidemiology of sudden death. Curr Cardiol Rep 2004; 6: 333-338.
52. Zhang, C L, McKinsey, T A, Chang, S, Antos, C L, Hill, J A, and Olson, E N Class II histone deacetylases act as signal-responsive repressors of cardiac hypertrophy. Cell 2002; 110: 479-488.
53. Antos, C L, McKinsey, T A, Dreitz, M, et al. Dose-dependent blockade to cardiomyocyte hypertrophy by histone deacetylase inhibitors. J Biol Chem 2003; 278: 28930-28937.
54. Kook, H, Lepore, J J, Gitler, A D, et al. Cardiac hypertrophy and histone deacetylase-dependent transcriptional repression mediated by the atypical homeodomain protein Hop. J Clin Invest 2003; 112: 863-871.
55. Shizukuda, Y, Piekarz, R L, Bates, S E, Sachdev, V, Finkel, T, and Rosing, D R Effect of a histone deacetylase inhibitor on human cardiac mass. Cardiovasc Drugs Ther 2005; 19: 89-90.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EQUIVALENTS

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

To give but a few examples, in the claims articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included unless otherwise indicated. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For example, in certain embodiments of the invention the biologically active agent is not an anti-proliferative agent. For purposes of brevity, all of the embodiments in which one or more elements, features, purposes, or aspects is excluded are not set forth explicitly herein.

What is claimed is:

1. A method for treating a peripheral T-cell lymphoma (PTCL) in a patient comprising intravenously administering to the patient a unit dose form of romidepsin over a time period of over 30 to 60 minutes.

2. The method of claim 1, wherein the romidepsin is administered over a time period of over 30 to 50 minutes.

3. The method of claim 1, wherein the romidepsin is administered over a time period of over 30 to 40 minutes.

4. The method of claim 1, wherein the unit dosage form contains from 0.5 to 28 mg/m2 of the romidepsin.

5. The method of claim 4, wherein the unit dosage form of romidepsin is 8 mg/m2, or 10 mg/m2, or 12 mg/m2, or 13 mg/m2, or 14 mg/m2.

6. The method of claim 1, wherein the romidepsin is administered on days 1, 8, and 15 of a 28-day cycle.

7. The method of claim 6, wherein the 28-day cycle is repeated for 3-10 times.

8. A method for treating a peripheral T-cell lymphoma (PTCL) in a patient comprising the steps of:
intravenously administering to the patient a unit dose form of romidepsin over a time period of over 30 to 60 minutes;
assessing serum potassium level in the patient;
assessing serum magnesium level in the patient;
administering potassium and/or magnesium to the patient if the serum potassium and/or magnesium concentration is below the normal range.

9. The method of claim 8, wherein potassium is administered to the patient if the serum potassium concentration is below 3.8 mEq/L.

10. The method of claim 8, wherein magnesium is administered to the patient if the serum magnesium concentration is below 1.9 mEq/L.

11. The method of claim 8, wherein the romidepsin is administered over a time period of over 30 to 50 minutes.

12. The method of claim 8, wherein the romidepsin is administered over a time period of over 30 to 40 minutes.

13. The method of claim 8, wherein the step of administering potassium and/or magnesium occurs prior to initiation of the romidepsin therapy.

14. The method of claim 8, wherein the step of administering potassium and/or magnesium occurs concurrently with initiation of the romidepsin therapy.

15. The method of claim 8, wherein the step of administering potassium and/or magnesium occurs following initiation of the romidepsin therapy.

16. The method of claim 8, wherein after administering potassium the serum potassium concentration in the patient reaches at least 3.5 mEq/L prior to initiation of the romidepsin therapy.

17. The method of claim 8, wherein after administering magnesium the serum magnesium concentration in the patient reaches at least 1.5 mEq/L prior to initiation of the romidepsin therapy.

18. The method of claim 8, wherein the romidepsin is administered as a unit dosage form, wherein said unit dosage form contains from 0.5 to 28 mg/m2 of the romidepsin.

19. The method of claim 18, wherein the unit dosage form of romidepsin is 8 mg/m2, or 10 mg/m2, or 12 mg/m2, or 13 mg/m2, or 14 mg/m2.

20. The method of claim 8, wherein the romidepsin is administered on days 1, 8, and 15 of a 28-day cycle, wherein the 28-day cycle is repeated for 3-10 times.

21. A method for treating a cutaneous T-cell lymphoma (CTCL) in a patient comprising intravenously administering to the patient a unit dose form of romidepsin over a time period of over 30 to 60 minutes.

22. The method of claim 21, wherein the romidepsin is administered over a time period of over 30 to 50 minutes.

23. The method of claim 21, wherein the romidepsin is administered over a time period of over 30 to 40 minutes.

24. The method of claim 21, wherein the unit dosage form contains from 0.5 to 28 mg/m$^2$ of the romidepsin.

25. The method of claim 24, wherein the unit dosage form of romidepsin is 8 mg/m$^2$, or 10 mg/m$^2$, or 12 mg/m$^2$, or 13 mg/m$^2$, or 14 mg/m$^2$.

26. The method of claim 21, wherein the romidepsin is administered on days 1, 8, and 15 of a 28-day cycle.

27. The method of claim 26, wherein the 28-day cycle is repeated for 3-10 times.

28. A method for treating a cutaneous T-cell lymphoma (CTCL) in a patient comprising the steps of:
intravenously administering to the patient a unit dose form of romidepsin over a time period of over 30 to 60 minutes;
assessing serum potassium level in the patient;
assessing serum magnesium level in the patient;
administering potassium and/or magnesium to the patient if the serum potassium and/or magnesium concentration is below the normal range.

29. The method of claim 28, wherein potassium is administered to the patient if the serum potassium concentration is below 3.8 mEq/L.

30. The method of claim 28, wherein magnesium is administered to the patient if the serum magnesium concentration is below 1.9 mEq/L.

31. The method of claim 28, wherein the romidepsin is administered over a time period of over 30 to 50 minutes.

32. The method of claim 28, wherein the romidepsin is administered over a time period of over 30 to 40 minutes.

33. The method of claim 28, wherein the step of administering potassium and/or magnesium occurs prior to initiation of the romidepsin therapy.

34. The method of claim 28, wherein the step of administering potassium and/or magnesium occurs concurrently with initiation of the romidepsin therapy.

35. The method of claim 28, wherein the step of administering potassium and/or magnesium occurs following initiation of the romidepsin therapy.

36. The method of claim 28, wherein after administering potassium the serum potassium concentration in the patient reaches at least 3.5 mEq/L prior to initiation of the romidepsin therapy.

37. The method of claim 28, wherein after administering magnesium the serum magnesium concentration in the patient reaches at least 1.5 mEq/L prior to initiation of the romidepsin therapy.

38. The method of claim 28, wherein the romidepsin is administered as a unit dosage form, wherein said unit dosage form contains from 0.5 to 28 mg/m2 of the romidepsin.

39. The method of claim 38, wherein the unit dosage form of romidepsin is 8 mg/m2, or 10 mg/m$^2$, or 12 mg/m$^2$, or 13 mg/m$^2$, or 14 mg/m$^2$.

40. The method of claim 28, wherein the romidepsin is administered on days 1, 8, and 15 of a 28-day cycle, wherein the 28-day cycle is repeated for 3-10 times.

* * * * *